(12) United States Patent
Furuya et al.

(10) Patent No.: US 12,067,891 B2
(45) Date of Patent: Aug. 20, 2024

(54) INFORMATION PROCESSING DEVICE, INFORMATION PROCESSING METHOD, AND PROGRAM

(71) Applicant: SONY GROUP CORPORATION, Tokyo (JP)

(72) Inventors: Shinichi Furuya, Tokyo (JP); Takanori Oku, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 680 days.

(21) Appl. No.: 17/287,787

(22) PCT Filed: Nov. 6, 2019

(86) PCT No.: PCT/JP2019/043379
§ 371 (c)(1),
(2) Date: Apr. 22, 2021

(87) PCT Pub. No.: WO2020/100671
PCT Pub. Date: May 22, 2020

(65) Prior Publication Data
US 2021/0383714 A1    Dec. 9, 2021

(30) Foreign Application Priority Data

Nov. 15, 2018  (JP) ................................. 2018-214531

(51) Int. Cl.
*G09B 15/06*       (2006.01)
*G02B 27/01*       (2006.01)
(Continued)

(52) U.S. Cl.
CPC .......... *G09B 15/06* (2013.01); *G02B 27/017* (2013.01); *G09B 5/00* (2013.01); *G09B 15/023* (2013.01);
(Continued)

(58) Field of Classification Search
CPC ........ G09B 15/06; G09B 5/00; G09B 15/023; G02B 27/017; G02B 2027/0138; G02B 2027/014; G10H 3/03
(Continued)

(56) References Cited

U.S. PATENT DOCUMENTS 5,728,960 A * 3/1998 Sitrick ...................... G10G 1/00
                                                    84/464 R
9,864,428 B2 * 1/2018 Zhang ...................... G06F 3/014
(Continued)

FOREIGN PATENT DOCUMENTS

AU      2011220382 A1 * 10/2012 ........... G02B 27/017
CN         1652203 A  *  8/2005
(Continued)

OTHER PUBLICATIONS

Merians et al., Strategies for Incorporating Bilateral Training into a Virtual Environment, 2007 IEEE/ICME International Conference on Complex Medical Engineering, May 23-27, 2007, pp. 1272-1276, Beijing, China.

*Primary Examiner* — Christina M Schreiber
(74) *Attorney, Agent, or Firm* — Paratus Law Group, PLLC

(57) ABSTRACT

There is provided an information processing device, an information processing method, and a program that can provide an information processing device, an information processing method, and a program that can effectively assist in learning performance. The information processing device includes a sensing data obtaining section configured to obtain sensing data regarding at least one of a motion pattern, a motion speed, a motion accuracy, and a motion amount of a motion element of a user in a practice in performance performed by movement of at least a part of a body of the user and a state of a result produced by the performance, an analyzing section configured to analyze the (Continued)

obtained sensing data and estimate information regarding the practice in the performance of the user on a basis of a result of the analysis, and an output section configured to output a result of the estimation to the user.

20 Claims, 27 Drawing Sheets

(51) Int. Cl.
    *G09B 5/00*            (2006.01)
    *G09B 15/02*         (2006.01)
    *G10H 3/03*          (2006.01)

(52) U.S. Cl.
    CPC ............... *G02B 2027/0138* (2013.01); *G02B 2027/014* (2013.01); *G10H 3/03* (2013.01)

(58) Field of Classification Search
    USPC .......................................................... 84/723
    See application file for complete search history.

(56) References Cited

U.S. PATENT DOCUMENTS

| | | | |
|---|---|---|---|
| 9,905,207 B2* | 2/2018 | Louhivuori | G10H 1/365 |
| 2003/0167908 A1* | 9/2003 | Nishitani | G10H 1/00 |
| | | | 84/723 |
| 2015/0268847 A1* | 9/2015 | Lane | G10G 1/00 |
| | | | 715/716 |
| 2015/0317910 A1* | 11/2015 | Daniels | G09B 9/00 |
| | | | 434/257 |
| 2017/0215495 A1* | 8/2017 | Okumiya | G01B 7/16 |
| 2017/0221377 A1* | 8/2017 | Uemura | G10H 1/0008 |
| 2020/0222756 A1* | 7/2020 | Sano | A61B 5/4088 |
| 2021/0104213 A1* | 4/2021 | Furuya | G09B 15/08 |
| 2021/0350773 A1* | 11/2021 | Furuya | G10G 3/04 |
| 2021/0383714 A1* | 12/2021 | Furuya | G09B 15/06 |
| 2022/0230556 A1* | 7/2022 | Grant | G09B 19/0038 |
| 2022/0398937 A1* | 12/2022 | Furuya | G09B 5/06 |
| 2023/0072423 A1* | 3/2023 | Osborn | G16H 20/30 |

FOREIGN PATENT DOCUMENTS

| | | | | |
|---|---|---|---|---|
| CN | 205486954 U | * | 8/2016 | |
| CN | 106371611 A | | 2/2017 | |
| CN | 110248601 A | * | 9/2019 | ............... A61B 5/00 |
| JP | H05-142987 A | | 6/1993 | |
| JP | H05142987 A | * | 6/1993 | |
| JP | 2000-089754 A | | 3/2000 | |
| JP | 2000089754 A | * | 3/2000 | |
| JP | 2000-293172 A | | 10/2000 | |
| JP | 2000293172 A | * | 10/2000 | |
| JP | 2009-047861 A | | 3/2009 | |
| JP | 2011-215856 A | | 10/2011 | |
| JP | 2011215856 A | * | 10/2011 | |
| JP | H05142987 A | * | 2/2013 | ............... F28D 1/02 |
| JP | 2013068879 A | | 4/2013 | |
| JP | 2016-080882 A | | 5/2016 | |
| JP | 2016080882 A | * | 5/2016 | ............ G09B 15/023 |
| JP | 2016116743 A | | 6/2016 | |
| JP | 2017-173589 A | | 9/2017 | |
| JP | 2017173589 A | * | 9/2017 | |
| WO | WO-2016092912 A1 | | 6/2016 | |
| WO | WO 2016/168117 A2 | | 10/2016 | |
| WO | WO-2016168117 A2 | * | 10/2016 | ............. G06F 1/163 |
| WO | WO-2018029171 A1 | | 2/2018 | |

\* cited by examiner

FIG. 16
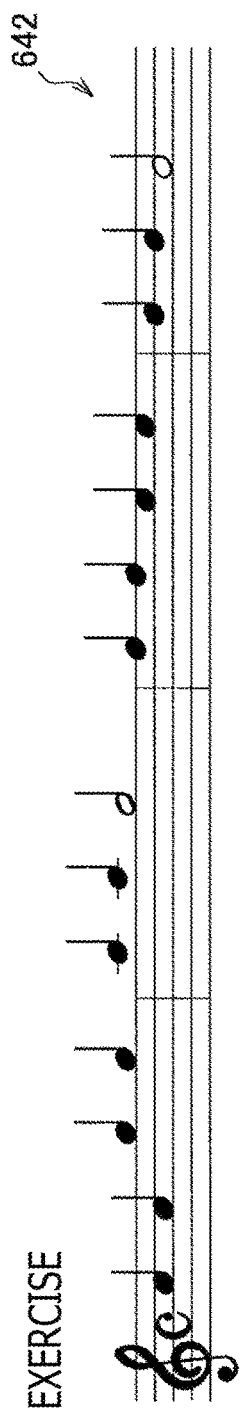
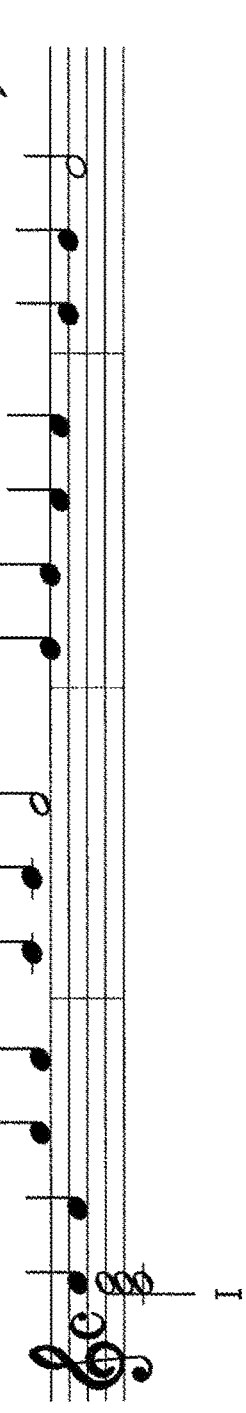

LEFT HAND FINGER GATHERING EXERCISE RANKING ON OCTOBER 31, 2018
3567 PARTICIPANTS

742

| FIRST PLACE | James | 97 POINTS |
| SECOND PLACE | Mary | 95 POINTS |
| THIRD PLACE | Robert | 90 POINTS |
| THIRD PLACE | Patricia | 90 POINTS |

744

YOUR RANKING IS 164TH PLACE, AND
YOU HAVE 67 POINTS.
THERE ARE 83 PEOPLE AT SAME PLACE.

INFORMATION PROCESSING DEVICE, INFORMATION PROCESSING METHOD, AND PROGRAM

CROSS REFERENCE TO PRIOR APPLICATION

This application is a National Stage Patent Application of PCT International Patent Application No. PCT/JP2019/043379 (filed on Nov. 6, 2019) under 35 U.S.C. § 371, which claims priority to Japanese Patent Application No. 2018-214531 (filed on Nov. 15, 2018), which are all hereby incorporated by reference in their entirety.

TECHNICAL FIELD

The present disclosure relates to an information processing device, an information processing method, and a program.

BACKGROUND ART

Recently, miniaturization, simplification, and the like of various kinds of motion sensors and biological information sensors have progressed. These sensors have therefore facilitated easy obtainment of various kinds of sensing data, and the various kinds of sensing data have come into use in assisting in learning performance (playing of a musical instrument, a sport, or the like) or the like, for example. A technology disclosed in the following PTL 1, for example, can be cited as an example of a technology that evaluates performance (playing of a musical instrument), and assists in the performance. In such learning assistance, information for the learning assistance can be presented by obtaining a variety of sensing data from a plurality of sensors, and analyzing the obtained plurality of pieces of sensing data.

CITATION LIST

Patent Literature

PTL 1

Japanese Patent Laid-Open No. 2009-47861

SUMMARY

Technical Problem

The present disclosure proposes an example of as information processing device, an information processing method, and a program that can effectively assist in learning performance.

Solution to Problem

According to the present disclosure, there is provided an information processing device including a sensing data obtaining section configured to obtain sensing data regarding at least one of a motion pattern, a motion speed, a motion accuracy, and a motion amount of a motion element of a user in a practice in performance performed by movement of at least a part of a body of the user and a state of a result produced by the performance, an analyzing section configured to analyze the obtained sensing data and estimate information regarding the practice in the performance of the user on the basis of a result of the analysis, and an output section configured to output a result of the estimation to the user.

In addition, according to the present disclosure, there is provided an information processing method including obtaining sensing data regarding at least one of a motion pattern, a motion speed, a motion accuracy, and a motion amount of a motion element of a user in a practice in performance performed by movement of at least a part of a body of the user and a state of a result produced by the performance, analyzing the obtained sensing data and estimating information regarding the practice in the performance of the user on the basis of a result of the analysis, and outputting a result of the estimation to the user.

Further, according to the present disclosure, there is provided a program for causing a computer to realize a function of obtaining sensing data regarding at least one of a motion pattern, a motion speed, a motion accuracy, and a motion amount of a motion element of a user in a practice in performance performed by movement of at least a part of a body of the user and a state of a result produced by the performance, a function of analyzing the obtained sensing data and estimating information regarding the practice in the performance of the user on the basis of a result of the analysis, and a function of outputting a result of the estimation to the user.

BRIEF DESCRIPTION OF DRAWINGS

FIG. 16 is an explanatory diagram (5) of assistance in explaining an example of a practice menu for the expression search learning.

FIG. 24 is an explanatory diagram (4) of assistance in explaining an example of the function improving training.

DESCRIPTION OF EMBODIMENT

Figure 1:
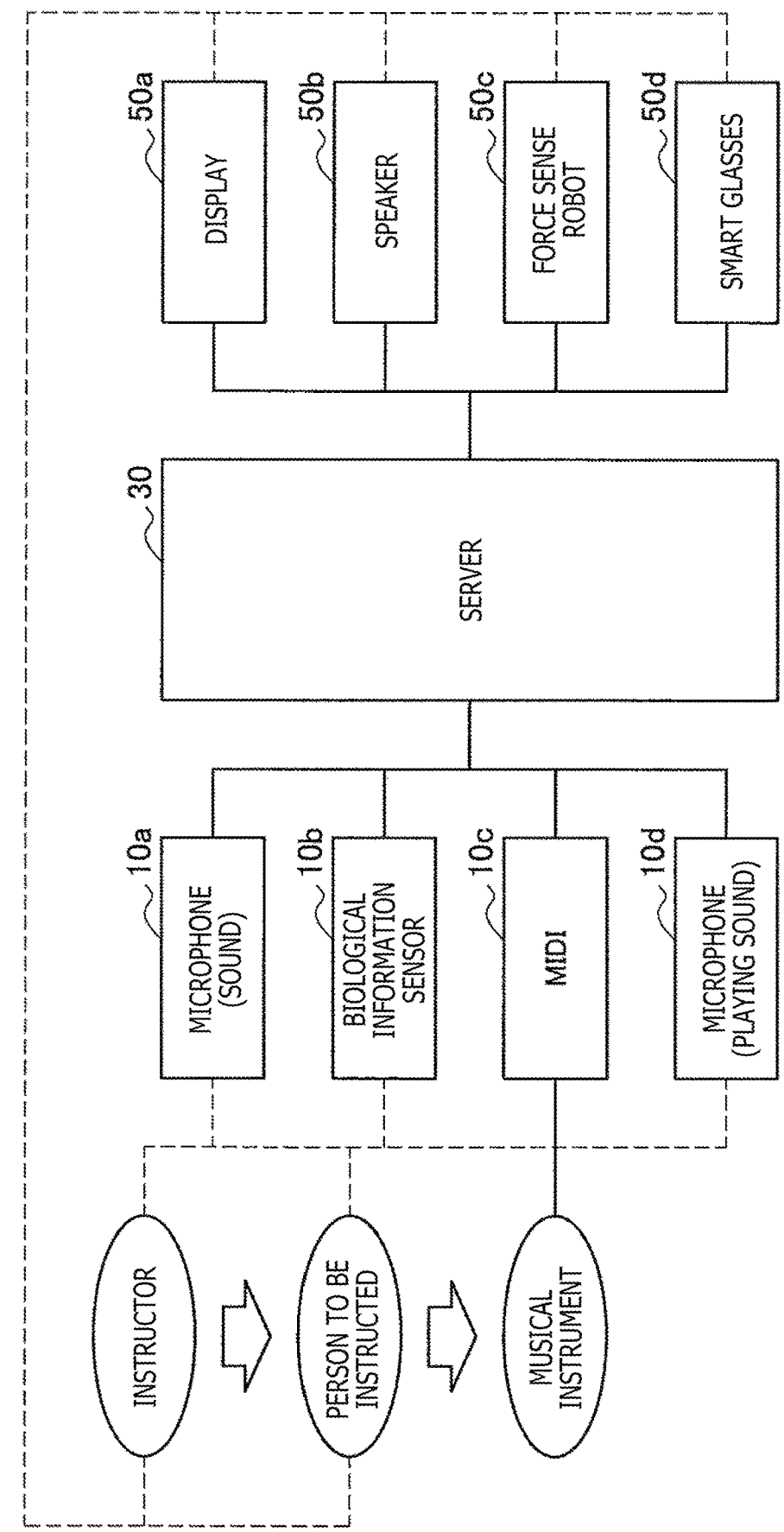
FIG. 1 is a diagram of assistance in explaining an example of a configuration of an information processing platform 1 according to an embodiment of the present disclosure.

A preferred embodiment of the present disclosure will hereinafter be described in detail with reference to the accompanying drawings. Incidentally, in the present specification and the drawings, constituent elements having substantially identical functional configurations are identified by the same reference signs, and thereby repeated description thereof will be omitted.

In addition, in the present specification and the drawings, a plurality of constituent element having substantially identical or similar functional configurations may be distinguished from each other by attaching different numbers following an identical reference numeral. However, in a case where each of the plurality of constituent elements having the substantially identical or similar functional configurations does not particularly need to be distinguished, only the identical reference numeral is attached. In addition, similar constituent elements of different embodiments may be distinguished from each other by attaching different alphabetic characters following an identical reference numeral. However, in a case where each of the similar constituent elements does not particularly need to be distinguished, only the identical reference numeral is attached.

Incidentally, description will be made in the following order.

1. Embodiment
   1.1. Outline of Information Processing Platform 1
   1.2. Configuration of Sensor device 10
   1.3. Example of Sensor Device 10
   1.4. Configuration of Server 30
   1.5. Configuration of Feedback Device 50
   1.6. Example of Feedback Device 50
   1.7. Information Processing Method
      1.7.1 Outline
      1.7.2 Generation of Portfolio
      1.7.3 Expression Search Learning
      1.7.4 Skill Search Practice
      1.7.5 Function improving Training
      1.7.6 Practice for Establishment in Memory
   1.8. Example of Presentation
2. Summary
3. Hardware Configuration
4. Supplement In addition, suppose in the following description that unless otherwise noted, users refer to a person to be instructed who practices and receives instruction with an objective of learning and improving a piano playing technique, an instructor who gives instruction to the person to be instructed, players from whom sensing data is collected in constructing a DB according to the present embodiment, and a provider providing service to the person to be instructed by using an information processing platform according to the present embodiment. Incidentally, in the following description, the information processing platform refers to an information processing platform including an information processing system and an environment in which the information processing system operates. More specifically, the information processing platform refers to an information processing platform including a server (including servers on a cloud), various kinds of sensor devices, applications incorporated in the server or the like, users (the instructor, the person to be instructed, the players, an administrator, and the like) using these, and an environment in which these can be used.

In addition, suppose in the following description that a degree of mastery, learning conditions, and a skill level in piano playing refer to the playing speed (tempo and rhythm) of a player in the playing, an accuracy of the playing (accuracy of rhythm or the volume of each sound), the volume of sound produced by the playing (peak of a sound waveform), reverberation of sound (integrated value of a sound waveform), a tone (spectrum), a volume difference or a time difference (what is called a "balance" in a chord (plurality of sounds)) between sounds in the chord, a difference (range) between a maximum value and a minimum value of each sound parameter, granularity (resolution) of the parameter of each sound, energy efficiency in the playing, and the like. Further, because there are parameters in tradeoff relation (for example, the speed and accuracy of the playing) among the plurality of parameters described above, the degree of mastery or the like in the piano playing may be the ratio of each parameter in consideration of such a case. In addition, the degree of mastery or the like may be an evaluation index based on subjective evaluation by a person (this player has a high accuracy or the like). In addition, in cases where the embodiment of the present disclosure is applied not only to piano playing but also to other movements, a degree of mastery, learning conditions, and a skill level in performance may be a motion pattern, a motion speed, a motion accuracy, a motion amount (a motion power, an impulse, a workload, and the like) of a motion element performed by a user, a state of a result produced by the performance, and the like.

Incidentally, the following description will include a case where an embodiment of the present disclosure is applied to assistance in learning a piano playing technique. However, the embodiment of the present disclosure is not limited to application to assistance in learning a piano playing technique, but can also be applied to assistance in learning a technique of playing another musical instrument or skills in sports or traditional arts, rehabilitation for a motor dysfunction, and the like. In addition, in the embodiment of the present disclosure, a musical instrument (target object) is not particularly limited to the acoustic piano either, but may be various kinds or electronic musical instruments (for example, electronic pianos and the like), or may be various kinds of acoustic musical instruments. Further, in the embodiment of the present disclosure, the target object related to a skill to be learned is not limited to a musical instrument, but may be a device including various kinds of sensors or a device used in combination with these sensors. For example, the above-described device may be a device including a sensor that detects virtual contact of a user with a projected object projected in a space by a projector. More specifically, the device can be a device including a sensor that detects contact with video of a musical instrument projected in a space in order for the user to virtually perform playing action on the video. In addition, the device may be play equipment imitating the shape of a musical instrument (game apparatus) (electronic apparatus related to playing). In this case, the device may include a sensor such as detects direct contact of the user or detects contact of the user via an object (for example, a stick or the like).

1. Embodiment

<1.1. Outline of Information Processing Platform 1>

A general configuration of an information processing platform 1 according to an embodiment of the present disclosure will first be described with reference to FIG. 1. FIG. 1 is a diagram of assistance in explaining an example of a configuration of the information processing platform 1 according to the present embodiment. As illustrated in FIG. 1, the information processing platform 1 according to the present embodiment includes various kinds of sensor devices 10 (for example, microphones 10a and 10d, a biological information sensor 10b, a MIDI (Musical Instrument Digital Interface) terminal 10c, and the like), a server 30, and feedback devices 50 (a display 50a, a speaker 50b, a force sense robot 50c, smart glasses 50d, and the like). These are communicatably connected to each other via a network. For example, the sensor devices 10, the server (information processing device) 30, and the feedback devices 50 may be connected to the above-mentioned network via a base station not illustrated or the like (for example, a base station for mobile telephones, an access point of a wireless LAN, or the like). That is, as a communication system used in the above-described network, a given system can be applied irrespective of whether the system is wired or wireless. An outline of each device included in the information processing platform 1 according to the present embodiment will be described in the following.

(Sensor Device 10)

A sensor device 10 can sense a state or the like related to a practice in performance by movement of a user (a person to be instructed or a player). Specifically, the sensor device 10 can be various kinds of biological information sensors 10b that can be fitted to a part of the body of the user, an imaging device (not illustrated) that images the user, a pressure sensor or a photoreflector sensor provided to a musical instrument such as a piano or the like played by the user, a microphone 10d that collects the sound of the piano, or the like. In addition, the sensor device 10 may be an electronic musical instrument itself such as an electronic piano or the like that can output a signal. In this case, sensing data is transmitted to the server 30 to be described later via the MIDI terminal 10c. Further, the sensor device 10 may be the microphone 10a that collects the voice of the instructor giving instruction to the person to be instructed. In this case, the voice of the instructor can be analyzed, and information as to what kind of instruction (advice) is given can be collected. Incidentally, the number and kinds of sensor devices 10 included in the information processing platform 1 according to the present embodiment are not particularly limited. For example, the sensor devices 10 may be various kinds of sensors fitted to commercially available musical instruments or the like in advance. Incidentally, details of the sensor devices 10 will be described later.

(Server 30)

The server 30 includes, for example, a computer or the like. Specifically, the server 30 can collect sensing data related to the playing (performance) of the user from the sensor devices 10, analyze and process the collected sensing data, feedback information for assistance is learning to the user or the like on the basis of a result of the analysis and the processing, and provide a suitable application (practice menu or the like). In addition, the server 30 may, for example, be a computer possessed by the user (for example, the person to be instructed, the instructor, the player) or the like, or may be a computer that provides service according to the present embodiment and is possessed by a service provider located at a place different from that of the player or the like. Further, the server 30 may be communicatably connected to a computer (not illustrated) possessed by another service provider performing other learning assistance service. Incidentally, details of the server 30 will be described later.

(Feedback Device 50)

A feedback device 50 is a device for providing the user or the like with feedback from the server 30 and an application. The feedback device 50 converts information to be provided into a visible form, a form of a force sense, a form of an auditory sense, or an audible form and provides the converted information during the playing of the user (person to be instructed) or after the playing, for example. For example, the feedback devices 50 may be a display device (display 50a) or an audio output device (speaker 50b), or may be a device such as a tablet, a smart phone, a laptop PC (Personal Computer), a notebook PC, or the like including the display device and the audio output device, or the like. Further, the feedback devices 50 may be a wearable device that can be fitted to a part of the body of the user (the person to be instructed or the player). More specifically, adoptable as the wearable device are wearable devices of various types such as an HMD (Head Mounted Display) type, an ear device (headphone) type, an anklet type, a bracelet type, a necklace type, an eyewear type (for example, the smart glasses 50*d*), a glove type (for example, the force sense robot 50*c*), a pad type, a badge type, a clothing type, or the like. Incidentally, details of the feedback devices 50 will be described later.

It is to be noted that while in FIG. 1, the information processing platform 1 according to the present embodiment is illustrated as including four sensor devices 10 and four feedback devices 50, the information processing platform 1 in the present embodiment is not limited to this. For example, the information processing platform 1 according to the present embodiment may include a plurality of sensor devices 10 and feedback device 50. Further, the information processing platform 1 according to the embodiment may include another communicating device or the like such as a relay device used at a time of transmitting sensing data from the sensor devices 10 to the server 30, for example.

<1.2. Configuration of Sensor Device 10>

Figure 2:
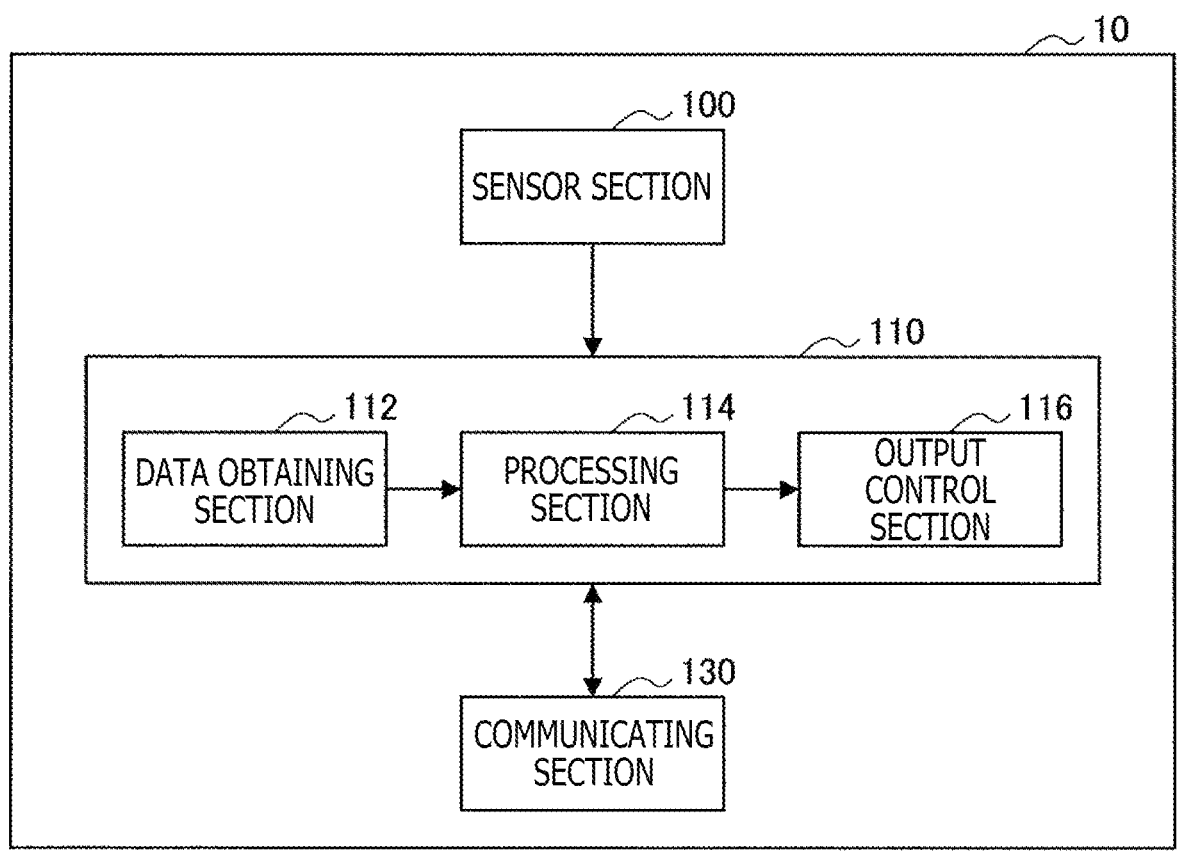
FIG. 2 is a block diagram illustrating a configuration of a sensor device 10 according to the same embodiment.

A configuration of the sensor device 10 according to the embodiment of the present disclosure will next be described with reference to FIG. 2. FIG. 2 is a block diagram illustrating a configuration of the sensor device 10 according to the present embodiment. As illustrated in FIG. 2, the sensor device 10 according to the present embodiment mainly includes a sensor section 100, a main control section 110, and a communicating section 130. Details of each functional section of the sensor device 10 will be described in the following.

(Sensor Section 100)

The sensor section 100 is, for example, fitted to the body of the user (the person to be instructed or the player), and is thereby able to obtain sensing data indicating the state of each motion element performed by each part of the body of the user during playing. The sensor section 100 is, for example, realized by one or a plurality of sensor devices such as an acceleration sensor, an angular velocity sensor, a gyro sensor, a geomagnetic sensor, a position sensor, a vibration sensor, a pressure sensor, a bending sensor, or the like. The sensor devices as described above detect changes in acceleration, angular velocity, or the like given by a motion element, and generate a plurality of pieces of sensing data indicating the detected changes. Further, the plurality of pieces of sensing data obtained by the sensor section 100 is output to the main control section 110 to be described later. In addition, the sensor section 100 may include a clock mechanism (not illustrated) acquiring an accurate time, and associate times at which the sensing data is obtained with the sensing data.

Incidentally, here, the bending sensor is, for example, a sensor using an element that, when bent, nonlinearly changes in a resistance value according to an amount of bending. When the bending sensor is fitted to a joint of the user (the person to be instructed or the player), for example, the bending sensor can detect the bending angle of the joint. In the present embodiment, when a sensor device as described above is fitted to each joint or the like of a finger, an arm, a leg, the body, and the like of the user, the attitude (inclination) of the finger and the arm within a space, moving speed thereof, the bending angle of the int, and the like can be detected quantitatively. Details of an example of such a bending sensor will be described later.

In addition, in the present embodiment, the sensor section 100 may be an imaging device that images the user (the person to be instructed or the player). In this case, the position and movement of the joint or the like of the user can be quantitatively detected by capturing the movement of the user or the like by a high-speed photographing camera (imaging device). Further, in the present embodiment, the movement of an eyeball of the user (eyeball motion) and the size of a pupil (pupil diameter) may be detected by the imaging device. In addition, in the present embodiment, the sensor section 100 may be an imaging device that is disposed within a musical instrument such as a piano or the like played by the user, and captures the movement of an action mechanism within the musical instrument (for example, hammers or the like hitting strings according to the movement of a keyboard in the case of the piano).

In addition, in the present embodiment, the sensor section 100 may be a nuclear magnetic resonance sensor that detects a state within an oral cavity of the user (the person to be instructed or the player) or within a trachea of the user (the person to be instructed or the player), the movement of lips or a tongue of the user (the person to be instructed or the player), or the like by using nuclear magnetic resonance. Specifically, the state, the movement, and the like described above can be detected when the user or the like performs playing within a magnetic resonance image device (MRI: Magnetic Resonance Imaging). Particularly in a case where the embodiment of the present disclosure is applied to techniques of playing various kinds of wind instruments (a flute, an oboe, a clarinet, a trumpet, and the like), the above-described MRI is useful because the lip or tongue movement, which is difficult to detect by another method, can be detected.

In addition, the sensor section 100 may be, for example, a keystroke detecting sensor that detects vertical movement of a piano keyboard (target object) moved by the movement (playing) of the user (the person to be instructed or the player). For example, the vertical movement of each keyboard can be detected by installing a keystroke detecting sensor under each keyboard. Specifically, the sensor section 100 can, for example, be a pressure sensor that detects a pressure applied to the piano keyboard by a motion element of the user or a photoreflector sensor including a light receiving and emitting sensor that detects the vertical movement of the keyboard on the basis of reflection of light. It is to be noted that in the present embodiment, the target object to be detected is not limited to the piano keyboard, but may be another musical instrument (an acoustic musical instrument or an electronic musical instrument) itself or a part of the other musical instrument.

In addition, the sensor section 100 may be a sound collecting device that collects sound from the piano played by the user (the person to be instructed or the player), that is, sound produced by the performance of the user. For example, the sensor section 100 may be the microphone 10*d* disposed in the vicinity of the piano or within the piano, or may be the microphone 10*a* that collects voice uttered by the person to be instructed or the player or voice uttered by the instructor instructing the person to be instructed. In the present embodiment, by collecting the voice uttered by the person to be instructed and the instructor, and performing voice recognition, it is possible to estimate, for example, what kind of practice the person to be instructed is performing or what kind of advice the instructor is giving or the like. Further, in the present embodiment, information obtained by the voice recognition may be stored as a study log in the server 30 to be described later.

Further, the sensing data from the sensor section 100 may be output (sound data) from an electronic musical instrument used according to the playing (operation) of the user (the person to be instructed or the player), that is, used in performance. In other words, in the present embodiment, the sensor section 100 may be the electronic musical instrument itself. In this case, the sensing data from the sensor section 100 is, for example, data in a digital format conforming to a MIDI standard which data is output from the MIDI terminal 10c. In addition, in the present embodiment, the sensor section 100 may be various kinds or sensors already provided to musical instruments (acoustic musical instruments or electronic musical instruments) already shipped by respective musical instrument manufacturers.

In addition, in the present embodiment, the sensor section 100 may be a biological information sensor such as a myoelectric sensor, a heartbeat sensor, a pulse sensor, a blood flow sensor, a respiration sensor, a brain wave sensor, a skin temperature sensor, a skin conductivity (skin resistance) sensor, a perspiration sensor, or the like that is fitted to a part of the body of the user (the person to be instructed or the player). Here, the myoelectric sensor is a sensor that detects a weak electric field occurring from muscle fibers constituting a muscle. Specifically, the myoelectric sensor can quantitatively detect an amount of muscle activity of a muscle by measuring, by a plurality of electrodes fitted to an arm of the user or the like, a myogenic potential based on an electric signal generated in the muscle fibers and propagated in a body surface when the muscle of the arm or the like contracts. In addition, the heartbeat sensor is a sensor that detect a heartbeat as pulsation in a heart. The pulse sensor is a sensor that detects a pulse as the pulsation of an artery which pulsation appears on a body surface or the like as a pressure change occurs in the inner wall of the artery when blood is sent through the whole body via the artery by pulsation in the heart (heartbeat). The blood flow sensor is a sensor that radiates infrared rays to the body, and detects a blood flow rate on the basis of reflection of the infrared light. Further, the respiration sensor can be a pneumotachograph that detects a change in respiration amount. The brain wave sensor is a sensor that has a plurality of electrodes fitted to a scalp, and detects a brain wave by extracting a periodic wave by removing noise from measured variations potential difference between the electrodes. The skin temperature sensor is a sensor that detects the body temperature of the user. The skin conductivity sensor is a sensor that detects the electric skin resistance of the user. In addition, the perspiration sensor is a sensor that detects the perspiration of the user.

Further, the sensor section 100 may include a position sensor such as a GPS (Global Positioning System) receiver or the like that obtains positional information of the user (the person to be instructed or the player). Such positional information may be used when the server 30 to be described later estimates what kind of practice the person to be instructed is performing or the like. In addition, the sensor section 100 may include various other kinds of sensors such as an atmospheric pressure sensor, a temperature sensor, a humidity sensor, and the like in order to obtain environmental information indicating the state of an environment in which the user plays. Such environmental information may be used when the server 30 predicts a change in a degree of mastery or a degree of fatigue of the person to be instructed.

(Main Control Section 110)

The main control section 110 is provided within the sensor device 10, and can control each block of the sensor device 10. The main control section 110 is, for example, realized by hardware such as a CPU (Central Processing Unit), a ROM (Read Only Memory), a RAM (Random Access Memory), and the like. In addition, the main control section 110 can also function as a data obtaining section 112, a processing section 114, and an output control section 116.

Details of these functions of the main control section 110 according to the present embodiment will be described in the following.

—Data Obtaining Section 112—

The data obtaining section 112 controls the sensor section 100, obtains sensing data output from the sensor section 100, and outputs the obtained sensing data to the processing section 114 to be described later. In addition, the data obtaining section 112 may include a clock mechanism (not illustrated) that acquires an accurate time, and associate a time at which the sensing data is obtained with the sensing data and output the sensing data to the processing section 114.

—Processing Section 114—

The processing section 114 converts the sensing data output from the data obtaining section 112 described above into a predetermined format that can be transmitted via the above-described network, and outputs the sensing data in the predetermined format to the output control section 116 to be described later.

—Output Control Section 116—

The output control section 116 transmits the sensing data in the predetermined format which sensing data is output from the processing section 114 described above to the server 30 by controlling the communicating section 130 to be described later.

(Communicating Section 130)

The communicating section 130 is provided within the sensor device 10, and is able to transmit and receive information to and from an external device such as the server 30 or the like. In other words, the communicating section 130 can be said to be a communication interface having a function of transmitting and receiving data. Incidentally, the communicating section 130 is realized by a communication device such as a communication antenna, a transmitting and receiving circuit, a port, or the like.

Incidentally, the sensor device 10 may be wearable devices of various types such as an HMD type, an ear device type, an anklet type, a bracelet type, a necklace type, an eyewear type, a pad type, a badge type, a belt type, a clothing type, and the like. Specifically, these wearable devices can be provided as motion capture to fingers, an arm portion, a leg portion, a trunk portion, a head portion, toes, or the like of the user (the person to be instructed or the player) in order to obtain various sensing data. In addition, the sensor device 10 may be a device installed in surroundings of the user such as an imaging device, a sound collecting device, or the like, or may be the musical instrument itself used by the user. The sensor device 10 is thus not particularly limited. Further, in the present embodiment, the sensor device 10 is not limited to the form as illustrated in FIG. 2.

<1.3. Example of Sensor Device 10>

Figure 3:
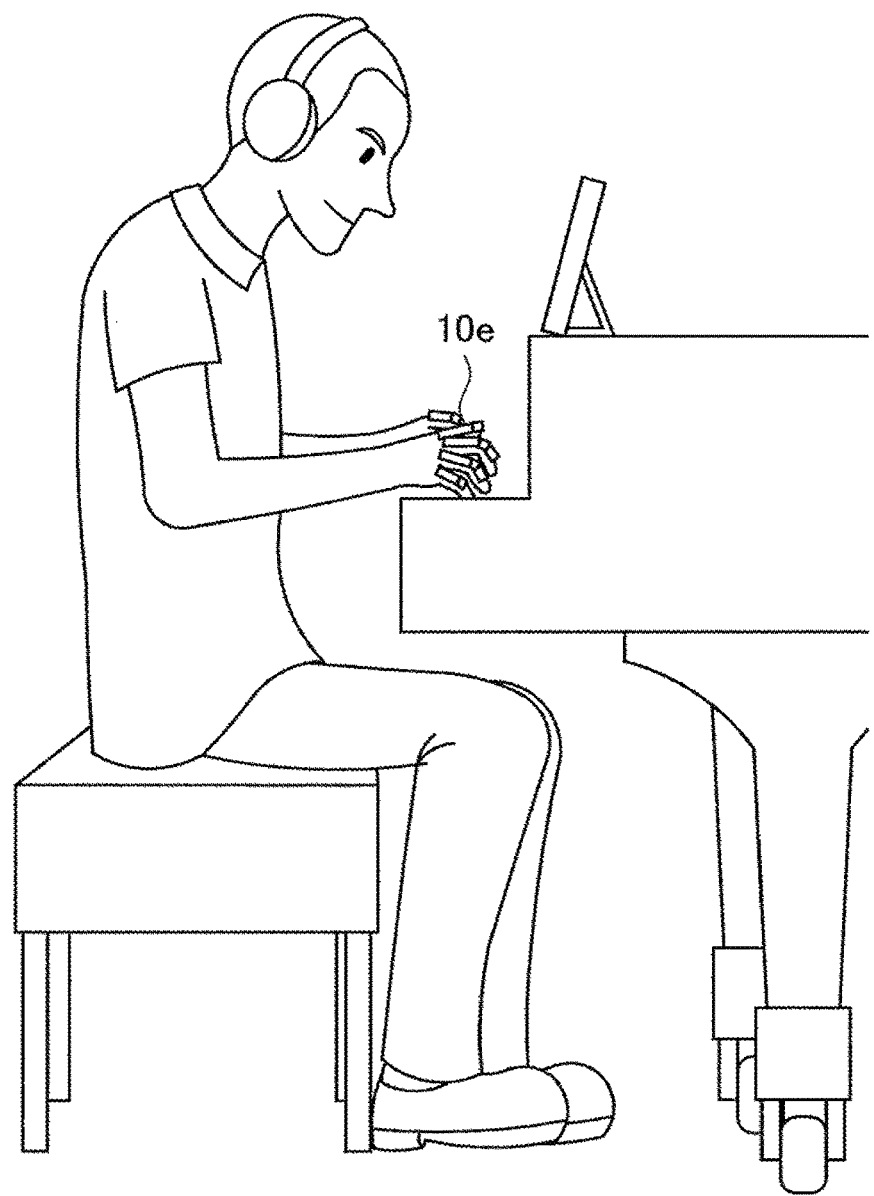
FIG. 3 is a diagram of assistance in explaining an example of wearing fingerstall type sensor devices 10e according to the same embodiment.
Figure 4:
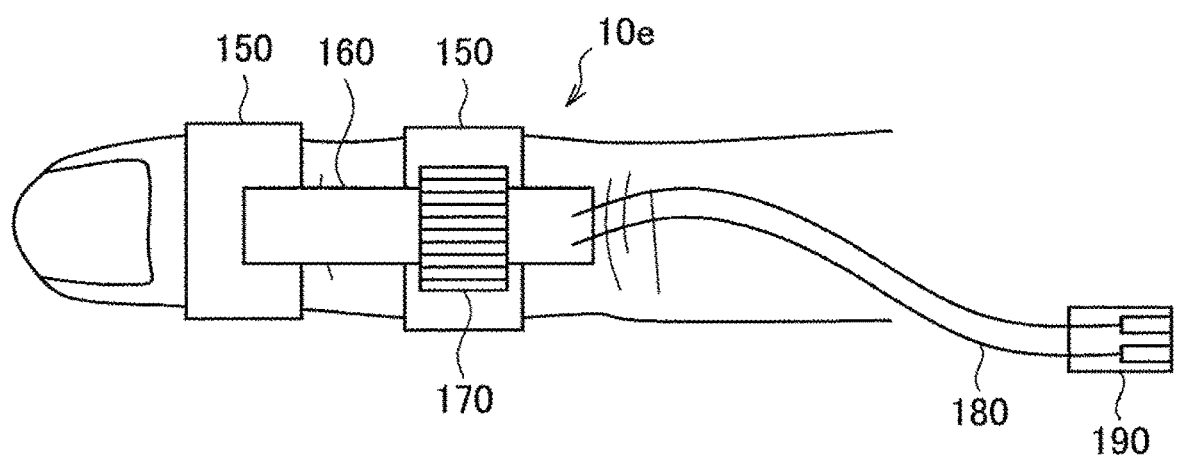
FIG. 4 is a top view of a fingerstall type sensor device 10e according to the same embodiment.
Figure 5:
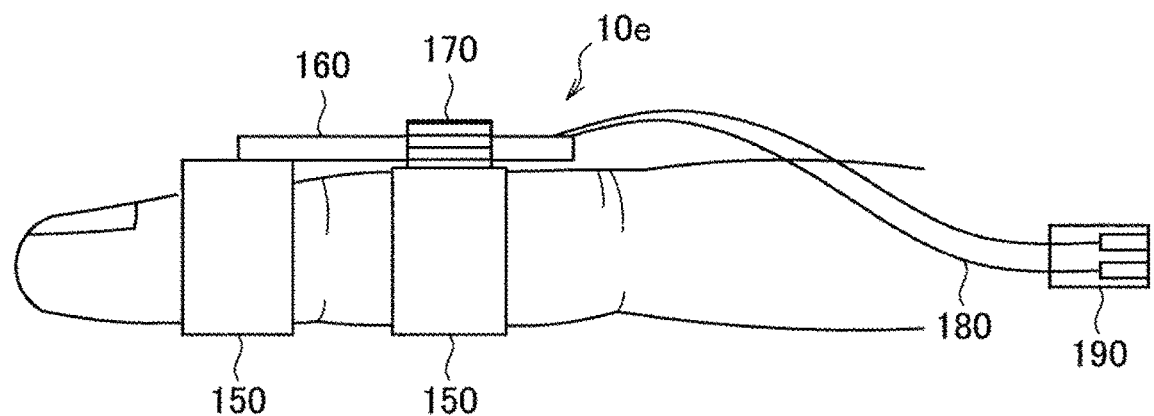
FIG. 5 is a side view of the fingerstall type sensor device 10e according to the same embodiment.

Here, referring to FIGS. 3 to 5, description will include a fingerstall type sensor device 10e as an example of the sensor device 10 according to the present embodiment. FIG. 3 is a diagram of assistance in explaining an example of wearing fingerstall type sensor devices 10e according to the present embodiment. FIG. 4 is a top view of a fingerstall type sensor device 10e according to the present embodiment. FIG. 5 is a side view of the fingerstall type sensor device 10e according to the present embodiment.

The fingerstall type sensor device 10e is an example or the bending sensor described above, and is a sensor that is fitted to a fingertip part or each digit of the user (the person to be instructed or the player) as illustrated in FIG. 3, and obtains sensing data related to the movement of the joint of each digit. Specifically, as illustrated in FIG. 4 and FIG. 5, the fingerstall type sensor device 10e includes a bending sensor member 160 that can detect bending of the joint of the digit by bending itself, and outputs the bending as an electric signal, and a ring member 150 that fixes the bending sensor member 160 to a fingertip. The fingerstall type sensor device 10e further includes a fixing member 170 that fixes the bending sensor member 160 to the ring member 150 in such a manner as to be capable of perturbation, wiring 180 that transfers an electronic signal from the bending sensor member 160, and a terminal 190 that outputs the electronic signal More specifically, the bending sensor member 160 is, for example, attached so as to straddle a distal phalanx and a middle phalanx of a fingertip of the user, and is able to detect the angle of the distal phalanx with respect to the middle phalanx, that is, bending of a distal interphalangeal joint.

It is to be noted that in the present embodiment, the bending sensor is not limited to such a form as to be fitted to the fingertip of the user, but may be a sensor in such a form as to be fitted to a part of the body of the user and able to detect the bending of various kinds of joints. According to such a fingerstall type sensor device 10e described above, sensing data regarding a motion element of the user can be obtained, and it is therefore possible to assist in imagery rehearsal or training for improving a motion function even in a state in which there is no musical instrument such as a piano or the like.

<1.4. Configuration of Server 30>

Figure 6:
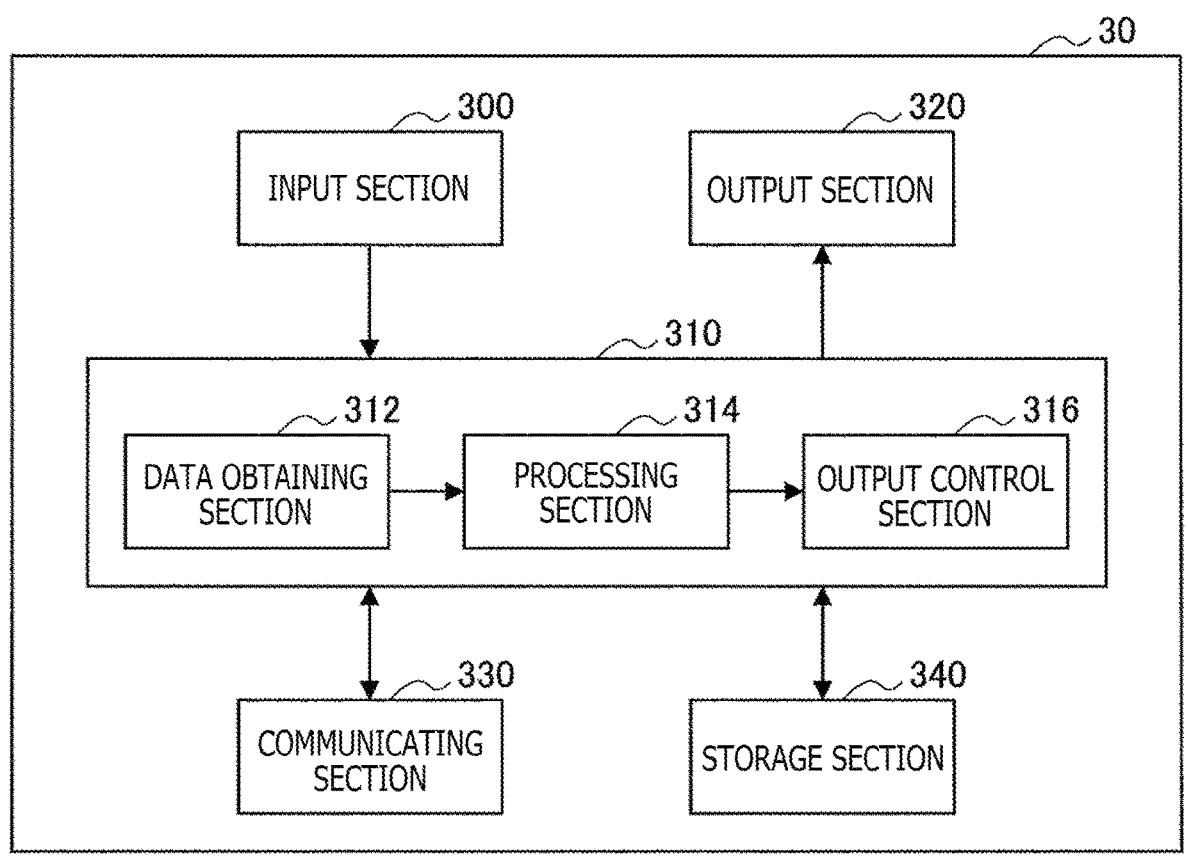
FIG. 6 is a block diagram illustrating a configuration of a server 30 according to the same embodiment.

A configuration of the server 30 according to the embodiment of the present disclosure will next be described with reference to FIG. 6. FIG. 6 is a block diagram illustrating a configuration of the server 30 according to the present embodiment. As described earlier, the server 30 includes, for example, a computer or the like. As illustrated in FIG. 6, the server 30 mainly includes an input section 300, a main control section 310, an output section 320, a communicating section 330, and a storage section 340. Details of each functional section of the server 30 will be described in the following.

(Input Section 300)

The input section 300 receives input of data and commands to the server 30. More specifically, the input section 300 is realized by a touch panel, a keyboard, or the like, and is able to receive attribute information of the user (the person to be instructed or the player) and input of practice content, advice, or the like of the person to be instructed or the instructor.

(Main Control Section 310)

The main control section 310 is provided within the server 30, and is able to control each block of the server 30. The main control section 310 is, for example, realized by hardware such as a CPU, a ROM, a RAM, and the like. In addition, the main control section 310 can also function as a data obtaining section (sensing data obtaining section) 312, a processing section (analyzing section) 314, and an output control section 316. Details of these functions of the main control section 310 according to the present embodiment will be described in the following.

—Data Obtaining Section 312—

The data obtaining section 312 obtains the sensing data transmitted from the sensor device 10 described above, and outputs the obtained sensing data to the processing section 314 to be described later. The sensing data is, for example, sensing data regarding at least one of a motion pattern, a motion speed, a motion accuracy, and a motion amount of a motion element, and sound in playing (performance) performed by movement of at least a part of the body of the user (the person to be instructed or the player), and a state of a result produced by the playing. The sensing data is obtained from the sensor device 10 described above. The data obtaining section 312 may further obtain also information input via the input section 300 described above.

—Processing Section 314—

The processing section 314 can analyze the sensing data obtained by the data obtaining section 312 and estimate information regarding practice in the performance on the basis of a result of the analysis. For example, the processing section 314 analyzes learning conditions of the playing (performance) of the user (the person to be instructed or the player) from the sensing data obtained by the data obtaining section 312 by using a predetermined algorithm, and for example, selects a practice menu to be performed by the user in the future on the basis of the learning conditions obtained by the analysis. The processing section 314 then outputs the content of the selected practice menu to the output control section 316 to be described later.

The processing section 314 analyzes learning conditions is playing of the user (the person to be instructed or the player) from the above-described sensing data. Further, on the basis of the learning conditions (for example, a skill that lacks in the user with respect to a target state or the like) obtained by the analysis, the processing section 314 selects a skill search practice menu including information regarding the content (practice menu) and a practice time of a skill search practice to be performed by the player in order for the user to attain a target value set in advance as well as timing and a break time or the like of a break to be taken by the user before and after the practice. Further, the skill search practice menu selected by the processing section 314 may include a training menu for improving a motion function or a sensory function related to the skill.

Further, on the basis of the learning conditions obtained by the analysis, the processing section 314 can select an expression search learning menu for the user (the person to be instructed or the player) to search more deeply for a playing expression. The expression search learning menu can, for example, make the user search for an expression by presenting playing data of another player of a musical piece related to the playing (performance), background information of the musical piece, interpretation information of the musical piece, composer information of the musical piece, data of another musical piece having a characteristic similar to the musical piece, and the like. Further, the expression search learning menu includes applying an effect to the playing sound of the user, which playing sound is obtained as the sensing data, according to an operation of the user, and enables a search for an expression by trying various effects. Incidentally, details of the expression search learning menu will be described later.

In other words, the processing section 314 can determine a schedule of the practice menu for the user on the basis of the learning conditions of the user. Incidentally, details of the practice menu selected by the processing section 314 will be described later.

Further, the processing section 314 may analyze the learning conditions of the playing (performance) of the person to be instructed and another player than the person to be instructed, convert these learning conditions into numerical values on the basis of a result of the analysis, and store the numerical values in the storage section 340 to be described later. Further, the processing section 314 may generate mastery ranking of a plurality of players or the like on the basis of the data of the thus obtained numerical values. When such ranking is presented to each player, the player himself/herself can easily recognize the level of the player, and can in turn enhance a motivation for performing practice to raise the position in the ranking. Incidentally, details of the generation of the ranking will be described later.

In addition, the processing section 314 may classify a practice performed by the user on the basis of the sensing data of the playing of the user (person to be instructed) which sensing data is stored in the storage section 340 to be described later, input information, or the like, and select a practice menu on the basis of a result of the classification. Incidentally, details of the classification of a practice will be described later.

More specifically, the processing section 314 can analyze the learning conditions of the user (person to be instructed) by selecting an appropriate algorithm according to a playing target state (for example, a desire to play fast or the like) set in advance by the user (the person to be instructed or the instructor), and applying the selected algorithm to the sensing data transmitted from the sensor device 10 (specifically the sensing data obtained during a practice). In addition, in the present embodiment, attribute information of each user (gender, age, height, weight, muscular strength, the size of a palm of a hand, the number of years of experience in piano playing, and the like) may be obtained, and the algorithm may be selected according to the attribute information. By making such a selection, it is possible to select a tailor-made practice menu according to the attributes of the user or the like. More specifically, in the present embodiment, the processing section 314 can analyze the learning conditions by referring to a DB (not illustrated) stored in the storage section 340, selecting the sensing data of the user to be analyzed and teacher data to be compared (for example, the sensing data of an excellent player serving as a model for the person to be instructed, sensing data obtained in playing when the person to be instructed himself/herself is in good condition, or the like) according to the target state and the attribute information described above, and comparing the selected data. At this time, the processing section 314 may calculate a difference between the sensing data of the user and the teacher data, a ratio of the sensing data of the user to the teacher data, a similarity of the sensing data of the user to the teacher data, or the like as numerically converted information indicating the learning conditions. Then, the processing section 314 can extract a skill or the like lacking in the user with respect to the target state by such analysis, and select a practice menu according to the extracted information.

Further, the processing section 314 may analyze a temporal, change in the learning conditions with respect to a practice time, and estimate a practice time necessary for the user (person to be instructed) to reach the target state. For example, the processing section 314 analyze a tendency of the temporal change in the learning conditions by plotting the temporal change in numerically converted learning conditions (for example, keystroke speed or the like) with respect to the practice time, and performing regression analysis. Further, the processing section 314 can estimate a practice time necessary to attain a target state (for example, a target keystroke speed) by performing extrapolation using the obtained tendency. In addition, the processing section 314 may analyze a temporal change in a motion function of the user with respect to the practice time by using the sensing data related to the motion function, and for example, estimate a degree of fatigue of a muscle or the like related to the motion function by comparing the temporal change in the motion function with a predetermined threshold value. Further, using regression analysis as in the above, the processing section 314 may estimate a practice time taken to reach a state in which the fatigue of the user accumulates and a possibility of injury is expected to increase, that is, to reach a state in which the temporal change in the motion function becomes lower than the predetermined threshold value. Then, the processing section 314 can determine the practice time as well as timing and a time for the user to take a break by using the thus estimated information. It is to be noted that in the present embodiment, the processing section 314 is not limited to estimation by the method as described above, but may, for example, analyze the tendency of the user by using machine learning as described later, and perform estimation on the basis of a result of the analysis.

Further, in the present embodiment, in order to obtain information for constructing the above-described DB, a large number of players (for example, approximately 100 players) are made to perform predetermined playing (a musical piece, a phrase, a scale, an arpeggio, a chord, or the like), and a large number of pieces of sensing data or the like are collected from the players during the playing by using sensor devices 10 described above. Then, in the present embodiment, the sensing data obtained as described above and playing state information or the like may be input to a learner (not illustrated) possessed by the processing section 314, and the learner may be made to perform machine learning. Specifically, suppose, for example, that the processing section 314 is provided with a supervised learner such as a support vector regression, a deep neural network, or the like. Then, the sensing data obtained from the sensor device 10 and a mastery level set in advance are respectively input as an input signal and a teacher signal (label) to the learner, and the learner performs multivariate analysis such as multiple regression analysis or the like and performs machine learning for relation between these pieces of information according to a predetermined rule. Then, using information obtained by such machine learning, the processing section 314 can analyze the learning conditions of the user (person to be instructed), select an algorithm for the analysis, select a practice menu, and estimate a practice time.

Output Control Section 316

The output control section 316 outputs, for example, a practice menu or the like as recommendation information for improving playing (performance) to the user (the person to be instructed or the instructor) on the basis of a result of analysis of the above-described processing section 314. For example, the output control section 316 can output the practice menu selected by the processing section 314 as the recommendation information. More specifically, a predetermined image is displayed by controlling a display section (display device) 570 of the feedback device 50, tactile stimulation is provided to the user by controlling a force sense mechanism (wearable device) 560 fitted to the body of the user, or a predetermined sound is output by controlling an audio output section (audio output device) 580. Incidentally, the output control section 316 may select a sense modality (a visual sense, an auditory sense, a tactile sense, or the like) suitable for output on the basis of the conditions of the user or the like. Thus, in the present embodiment, efficient performance learning assistance can be realized because the recommendation information can be provided to the user in a sense modality corresponding to the conditions of the user or the like.

(Output Section 320)

The output section 320 includes, for example, a display, a speaker, a video output terminal, an audio output terminal, or the like. The output section 320 outputs various kinds of information by images, sound, or the like.

(Communicating Section 330)

The communicating section 330 is disposed within the server 30. The communicating section 330 can transmit and receive information to and from an external device such as the sensor device 10, the feedback device 50, or the like. Incidentally, the communicating section 330 is realized by a communication device such as a communication antenna, a transmitting and receiving circuit, a port, or the like.

(Storage Section 340)

The storage section 340 is disposed within the server 30. The storage section 340 stores a program, information, and the like for the above-described main control section 310 to perform various kinds of processing as well as information obtained by the processing. Incidentally, the storage section 340 is, for example, realized by a magnetic recording medium such as a hard disk (Hard Disk: HD) or the like, a nonvolatile memory such as a flash memory or the like, or the like.

<1.5. Configuration of Feedback Device 50>

Figure 7:
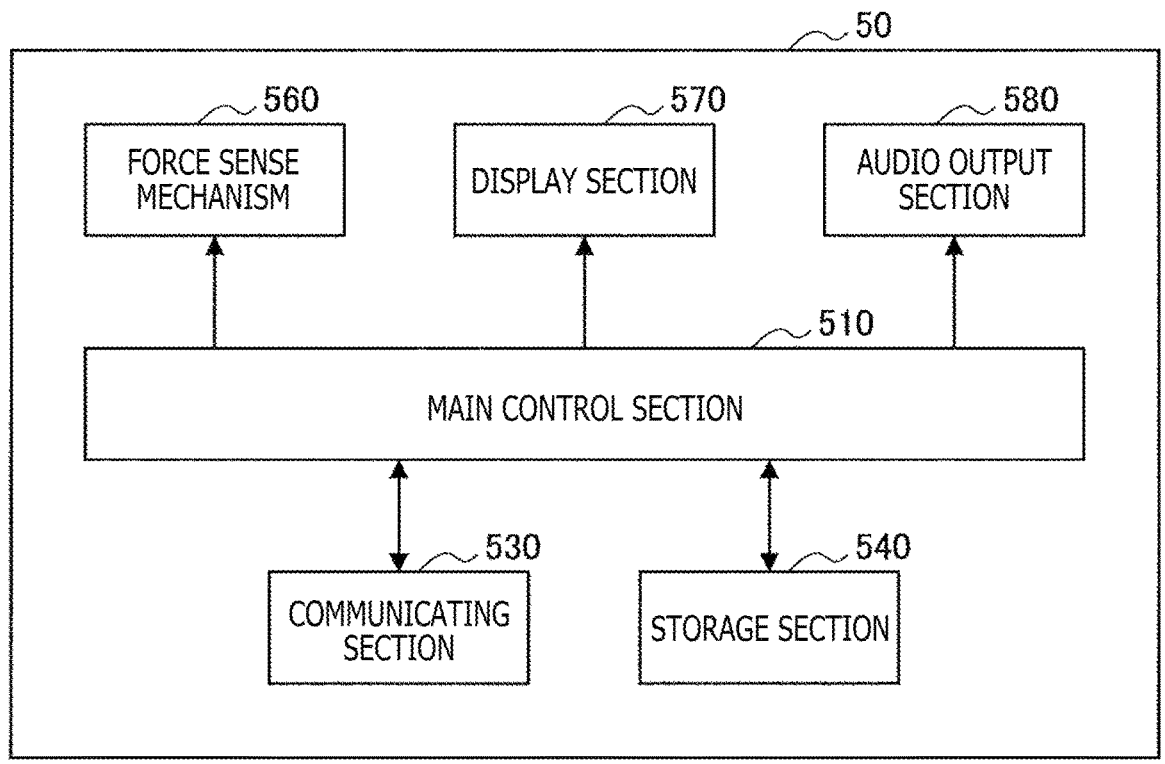
FIG. 7 is a block diagram illustrating a configuration of a feedback device 50 according to the same embodiment.
Figure 8:
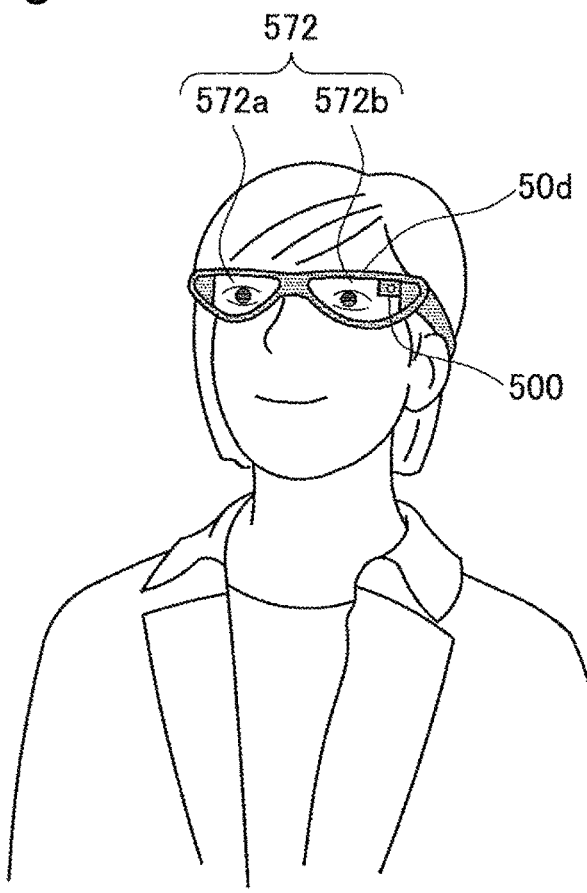
FIG. 8 is as explanatory diagram of assistance in explaining smart glasses 50d according to the same embodiment.

A configuration of the feedback device 50 according to the embodiment of the present disclosure will next be described with reference to FIG. 7 and FIG. 8. FIG. 7 is a block diagram illustrating a configuration of the feedback device 50 according to the present embodiment. FIG. 8 is an explanatory diagram of assistance in explaining the smart glasses 50*d* according to the present embodiment.

As described earlier, the feedback device 50 can be a device such as a tablet, a laptop PC, a notebook PC, a wearable device, or the like. In addition, as illustrated in FIG. 7, the feedback device 50 mainly includes a main control section 510, a communicating section 530, a storage section 540, a force sense mechanism 560, a display section 570, and an audio output section 580. Details of each functional section of the feedback device 50 will be described in the following.

(Main Control Section 510)

The main control section 510 is disposed within the feedback device 50, The main control section 510 can control each block of the feedback device 50. The main control section 510 is, for example, realized by hardware such as a CPU, a ROM, a RAM, and the like.

(Communicating Section 530)

The communicating section 530 can transmit and receive information to and from an external device such as the server 30 or the like. Incidentally, the communicating section 530 is realized by a communication device such as a communication antenna, a transmitting and receiving circuit, a port, or the like.

(Storage Section 540)

The storage section 540 is disposed within the feedback device 50. The storage section 540 stores a program and the like for the above-described main control section 510 to perform various kinds of processing as well as information obtained by the processing. Incidentally, the storage section 540 is, for example, realized by a magnetic recording medium such as an HD or the like, a nonvolatile memory such as a flash memory or the like, or the like.

(Force Sense Mechanism 560)

The force sense mechanism 560 is a device that transmits a force sense such as an application of a force or the like to a part (joint or the like) of the body of the user (person to be instructed) on the basis of information transmitted from the server 30. For example, the force sense mechanism 560 can be a glove type wearable device (wearable device) (not illustrated) fitted to a hand of the user. Specifically, the glove type wearable device is referred to as a finger exoskeleton robot, and includes a mechanism including a plurality of exoskeleton members (not illustrated) and an actuator (an electric actuator, a pneumatic actuator, or the like) (not illustrated) that can move each of the exoskeleton members. The glove type wearable device applies a force to a finger or a joint of the user by operating an exoskeleton member by the above-described actuator, and thus, for example, makes the person to be instructed have a haptic perception of an amount of excess or shortage of a force in the extending and bending direction of the joint or the like. In addition, in the present embodiment, the above-described sensor device 10 may be fitted to the force sense mechanism 560. In this case, the force sense mechanism 560 may apply a force or a stimulus to a part of the body of the user such that the above-described sensor device 10 obtains a target value.

In addition, in the present embodiment, the force sense mechanism 560 may, for example, be a vibrating device that applies vibration to a part of the body of the user (person to be instructed) or a stimulating device that uses an electric muscle stimulus as a stimulus applied to a muscle. That is, in the present embodiment, it suffices for the force sense mechanism 560 to be able to feedback information to the user in a sensible manner (biofeedback) by applying tactile stimulation to a part of the body of the user. According to the force sense mechanism 560, it is possible to assist in imagery rehearsal of the user even without a musical instrument such as a piano or the like.

(Display Section 570)

The display section 570 is a device for displaying information for the user (person to be instructed). The display section 570, for example, outputs the information by an image or light to the user. The display section 570 is realized by a display (not illustrated), a light emitting element (not illustrated), or the like. Further, the display section 570 may be realized by a video output terminal or the like. More specifically, the display section 570 may be a projecting device that displays a predetermined virtual object as augmented reality (AR) in such a manner as to be superimposed on a real space. The virtual object in this case may schematically represent a plurality of spectators or the inside of a piano (musical instrument) played (operated) by the user. Incidentally, details of a concrete example of display using augmented reality will be described later.

(Audio Output Section 580)

The audio output section 580 is a device for audio output of information to the user (the person to be instructed or the instructor). The audio output section 580 may, for example, be headphone speakers (not illustrated) fitted to the ears of the user or a speaker (not illustrated) disposed in the vicinity of the user. Further, the audio output section 580 may be realized by an audio output terminal or the like.

In addition, the feedback device 50 may have an input section not illustrated. The input section has a function of receiving input of data and commands to the feedback device 50. More specifically, the input section is realized by a touch panel, a button, a switch, a key, a keyboard, a microphone, an image sensor, and the like.

In addition, in the present embodiment, the functions of the sensor section 100 of the sensor device 10 and the force sense mechanism 560 or the like of the feedback device 50 may be integrated into one wearable device.

<1.6. Example of Feedback Device 50>

As described earlier, the display section 570 may be a projecting device that can display an object based on information from the server 30 as augmented reality (AR) in such a manner as to be superimposed on a real space. Such a projecting device can, for example, be the smart glasses 50*d* fitted in front of the eyes of the user (person to be instructed). The smart glasses 50*d* are provided with a transmissive display. The transmissive display, for example, retains a virtual image optical system including a transparent light guiding unit or the like in front of the eyes of the user by using a half-silvered mirror or a transparent light guide plate, and displays the above-described object on the inside of the virtual image optical system. In addition, the above-described projecting device may be an HMD fitted to a head portion of the user.

Specifically, as illustrated in FIG. 8, the smart glasses 50*d* are, for example, fitted to the head portion of the user (person to be instructed), and have a display unit 572 corresponding to eyeglass lens parts positioned in front of the eyes of the user when worn. The display unit 572 may be a transmissive display that allows the outside of the eyeglass lens parts to be viewed or a non-transmissive display that does not allow the outside of the eyeglass lens parts to be viewed. Incidentally, in the following description, the projecting device having the display unit 572 of the transmissive display will be referred to as "smart glasses." The display unit 572 can present a virtual object in front of the eyes of the user by displaying the virtual object. Incidentally, in the following description, the virtual object refers to a virtual object that can be perceived like a real object present in the real space by the user. Further, the present embodiment is not limited to a form of displaying the virtual object for both eyes of the user, but may have a form of displaying the virtual object only for one eye of the user.

More specifically, as illustrated in FIG. 8, the smart glasses 50*d* have a configuration such that a pair of a display unit 572*a* and a display unit 572*b* for a left eye and for a right eye is disposed in front of the eyes of the user (person to be instructed). Transmissive displays, for example, are used as the display units 572*a* and 572*b*. The smart glasses 50*d* can set the displays in a through state, that is, a transparent or semitransparent state by controlling the transmittance of the transmissive displays. In addition, because the display units 572*a* and 572*b* are set in a through state, even in a case where the smart glasses 50*d* are worn at all times as with eyeglasses, the user can perceive the surrounding real space, so that normal life, playing action, or the like of the user not hindered. Further, the display units 572*a* and 572*b* can display an image of text, a figure, or the like while the through state is maintained, that is, can display the virtual object as augmented reality (AR) in such a manner as to be superimposed on the real space. Such transmissive displays, for example, retain a virtual image optical system including a transparent light guiding unit or the like in front of the eyes of the user by using a half-silvered mirror or a transparent light guide plate, and display the virtual object on the inside of the virtual image optical system.

Incidentally, in the present embodiment, in a case where non-transmissive displays are used, the display unit 572 may display the virtual object in such a manner as to be superimposed on an captured image of the real space imaged by a camera 500 disposed in the smart glasses 50*d* while displaying the captured image of the real space.

Further, in the present embodiment, the display unit 572 may be realized as an LED (Light Emitting Diode) light source or the like that directly projects video on the retinas of the user (person to be instructed). That is, the feedback device 50 may be realized as a projection type HMD.

<1.7. Information Processing Method>

The above description has been made in detail of the information processing platform 1 according to the present embodiment and the configurations of the sensor device 10, the server 30, and the feedback device 50 included in the information processing platform 1. An information processing method according to the present embodiment will next be described.

(1.7.1 Outline)

Figure 9:
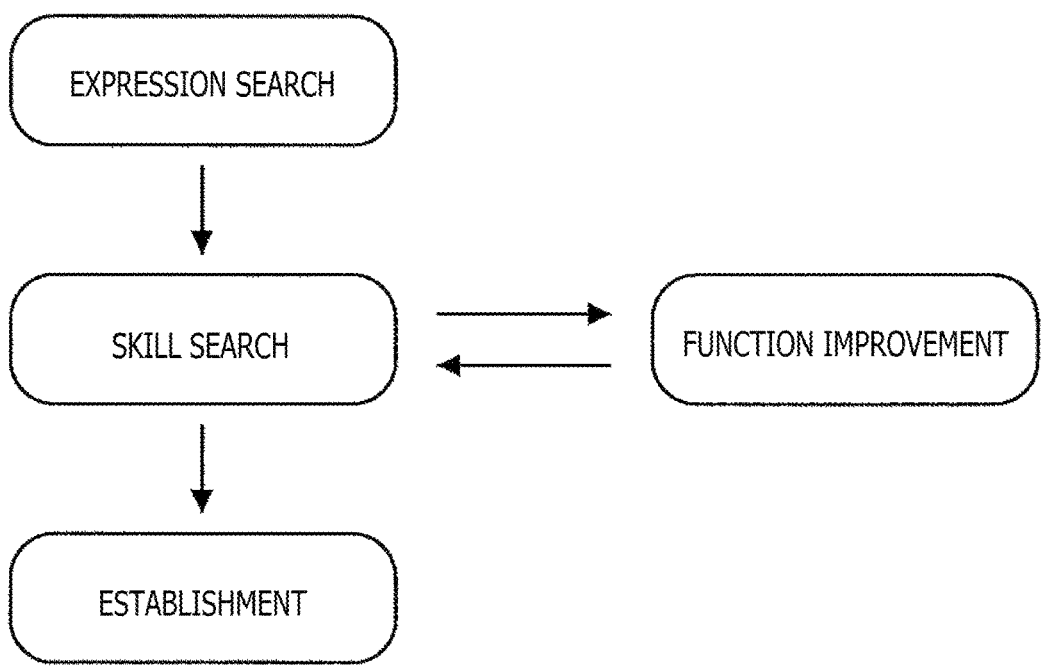
FIG. 9 is an explanatory diagram of assistance in explaining an outline of learning assistance provided by an application according to the same embodiment.
Figure 10:
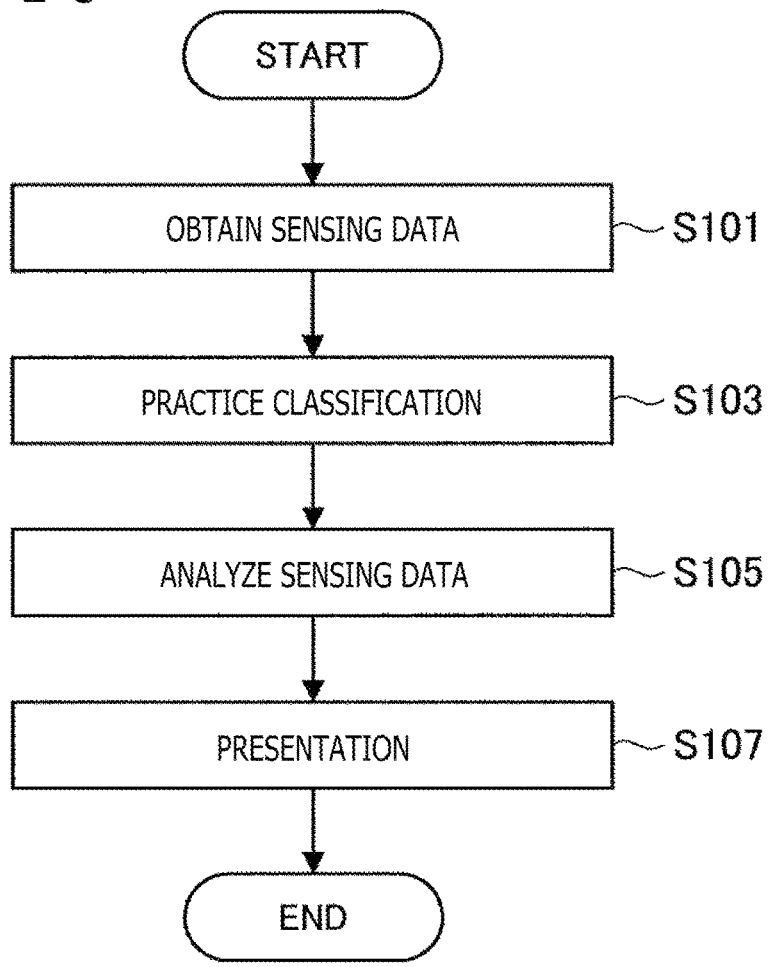
FIG. 10 is a flowchart of assistance in explaining an example of an information processing method according to the same embodiment.

As described earlier, the information processing platform 1 according to the present embodiment can provide an application such as a practice menu or the like that assists in learning playing (performance) of the piano. An outline of the application will be described with reference to FIG. 9 and FIG. 10. FIG. 9 is an explanatory diagram of assistance in explaining an outline of learning assistance provided by the application according to the present embodiment. FIG. 10 is a flowchart of assistance in explaining an example of the information processing method according to the present embodiment.

It is assumed in the present embodiment that as illustrated in FIG. 9, in order to learn (improve) the playing of the piano, the person to be instructed is, for example, desired to perform three practices, that is, expression search learning in which a search is made for an expression related to the playing, a skill search practice in which a search is made for a skill related to the playing, and a practice that makes the skill or the like obtained as a result of the search established in the body of the person to be instructed. Specifically, an expression search is a process of finding an element desired for the person to be instructed to express a desired image, and a skill search is a process of learning a skill desired for the person to be instructed to express the desired image. Further, an establishing practice is a process of making a desired expression established in the body of the person to be instructed so as to be able to be reproduced at all times by practicing repetitively. In addition, in the present embodiment, in the skill search practice that makes a search for a skill, training for improving a motion function or the like related to the learning of the skill is preferably performed as required. The present embodiment to be described in the following can provide various kinds of applications (a practice menu, training, a game, and the like) that can assist the person to be instructed in learning a piano playing technique on the basis of the assumption as described above.

Specifically, in the present embodiment, an information processing method as illustrated in FIG. 10 is performed. The information processing method includes a plurality of steps from step S101 to step S107. An outline of each step included in the information processing method according to the present embodiment will be described in the following.

—Step S101—

In this step S101, the server 30 obtains various kinds of sensing data during practices of the user (person to be instructed). Incidentally, suppose that the sensing data includes information input from the user (for example, input of practice content or the like).

—Step S103—

In this step S103, the server 30 analyzes the sensing data obtained in the above-described step S101, and classifies the practices performed by the user (person to be instructed). Specifically, the server 30 classifies the practices performed by the user into kinds of practices, that is, expression search learning, a skill search practice in which a search is made for a skill related to playing, an establishing practice, and ability improving training, calculates a practice time of each classification, and generates a portfolio to be described later. The generated portfolio is used when the server 30 selects a practice menu (for example, the server 30 selects a type of practice that the user has not sufficiently performed).

—Step S105—

In this step S105, the server 30 analyzes the sensing data obtained in the above-described step S101, and estimates the learning conditions of the user (person to be instructed) as well as a practice menu and a practice time necessary to attain a target state. In addition, on the basis of the analysis of the sensing data, the server 30 may estimate a fatigue of a muscle or the like related to a motion function of the user, and estimates timing in which the user is to take a break and a break time. Then, together with such estimations, the server 30 refers also to the portfolio obtained in step S103, and selects a practice menu to be presented to the user.

—Step S107—

In this step S107, the server 30 presents the practice menu selected in the above-described step S105 to the user (person to be instructed). Details of a form of presentation will be described later. However, in this step S107, the practice menu, the practice time and the break time to be taken by the user, and the like are presented, or advice to the user and the like are presented. Further, this step S107 may, for example, present the sensing data obtained in step S101, various kinds of indexes based on the sensing data, the portfolio obtained in step S103, and the learning conditions obtained in step S105, temporal changes in the learning conditions, and the like.

(1.7.2 Generation of Portfolio)

Figure 11:
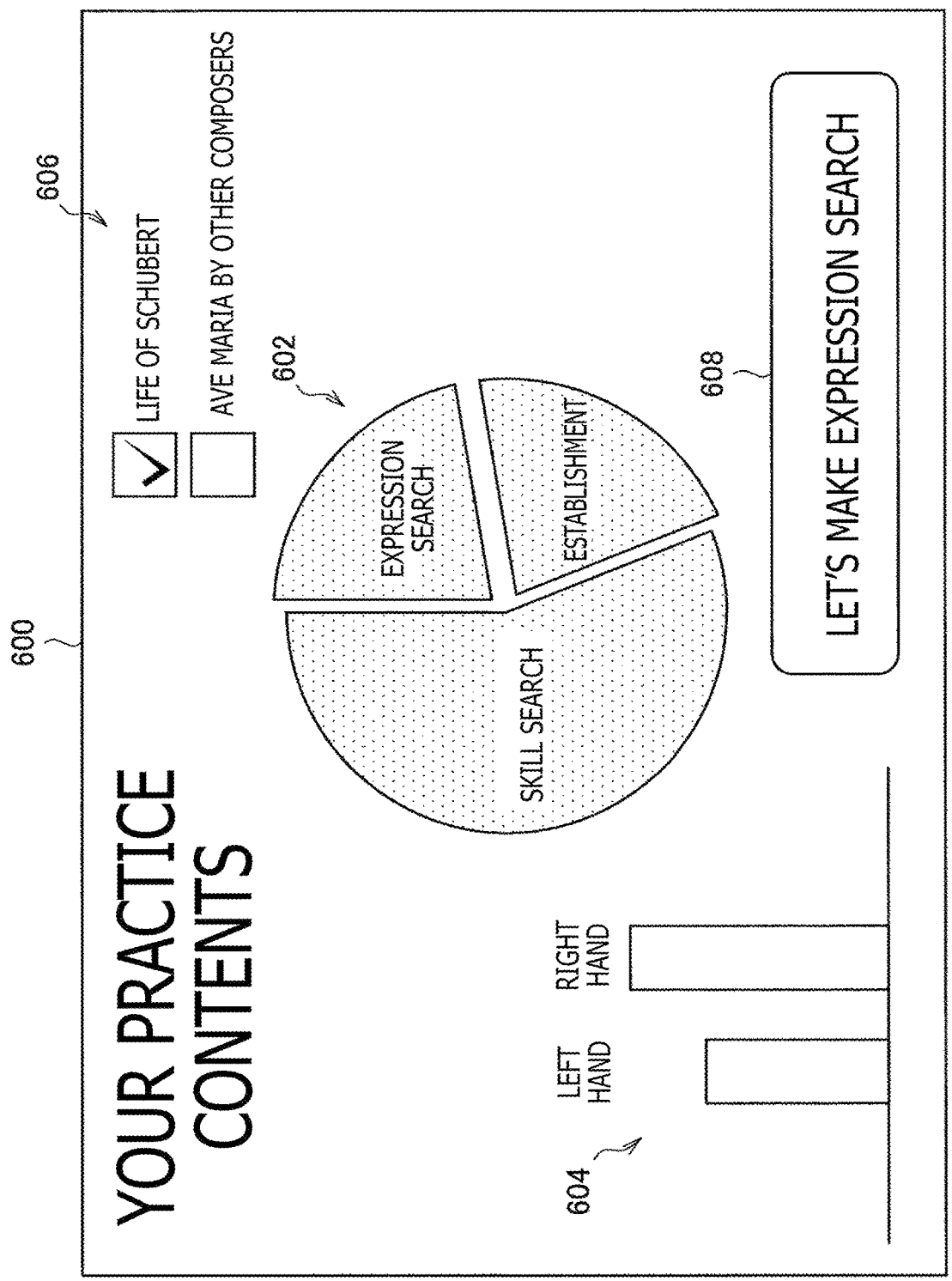
FIG. 11 is an explanatory diagram of assistance in explaining an example of presentation of a portfolio according to the same embodiment.

Generation of the above-described portfolio will next be described with reference to FIG. 11. FIG. 11 is an explanatory diagram of assistance in explaining an example of presentation of the portfolio according to the present embodiment. In the present embodiment, as described earlier, the practices performed by the user (person to be instructed) are classified, practice times of respective classifications are calculated, and a portfolio is generated. According to the present embodiment, when the practices are classified, and consecutively obtained times of the classified practices and the like are visualized, the user (the person to be instructed or the instructor) can easily recognize what kind of practice is lacking.

Specifically, in the present embodiment, the user (the person to be instructed or the instructor) may input what kinds of practices are performed in daily practice on an application. At the same time, the user may input a point that the user noticed during the practice, a point to be noted, and the like on the application. These pieces of input information are stored as a study log in the server 30. In addition, in the present embodiment, what kind of practice has been performed may be estimated by collecting an uttered voice uttered by the user during the practice, and performing voice recognition of the collected audio data, and information obtained by the voice recognition (for example, advice extracted from the voice or the like) may be stored as a study log in the server 30. Further, in the present embodiment, what kind of practice has been performed may be estimated by collecting playing sound produced by a musical instrument such as a piano or the like played by the person to be instructed during the practice, and analyzing the collected sound data. That is, in the present embodiment, the voices, playing sound, and the like of the person to be instructed and the instructor may be collected as sound related to the practice in playing (performance) of the non-instructor or the like, and the practice may be estimated on the basis of the collected sound. In addition, in the present embodiment, the server 30 may estimate what kind of practice has been performed by analyzing sensing data obtained by various kinds of sensor devices 10.

Then, as illustrated in FIG. 11, the server 30 classifies the practices performed by the user (person to be instructed), calculates the practice times of respective classifications, and generates and displays a portfolio. Specifically, a screen display 600 presenting the portfolio displays a circle graph 602 indicating ratios of the practice times of the respective classified practices. The circle graph 602 illustrated in FIG. 11 displays the ratios of the practice times of expression search learning, a skill search practice in which a search is made for a skill related to playing, and an establishing practice, which practices have been performed by the user. According to such a circle graph 602, the user can clearly realize an excess and a shortage or an imbalance of the own practices.

Further, in the present embodiment, as illustrated in FIG. 11, a bar graph 604 indicating which hand has attained a higher degree of mastery of a skill and a title display 606 indicating what kind of learning has been performed in the expression search learning or the like may be included. In addition, in the present embodiment, as illustrated in FIG. 11, the server 30 may extract a practice that is lacking, and illustrate a display 608 including words recommending the user (person to be instructed) performing the practice that is lacking on the basis of extracted content.

According to the present embodiment, the presentation of the portfolio enables the user (the person to be instructed or the instructor) to easily recognize what kind of practice is lacking. Further, according to the present embodiment, the practice that is lacking can be recognized easily even when the instructor does not attend the practice of the person to be instructed, and therefore instruction can be given even in a case where the person to be instructed is located at a remote place (for example, consulting or the like).

In addition, as described earlier, in the above-described step S107, the server 30 presents a practice menu and advice according to the learning conditions of the person to be instructed. Accordingly, in the following, content (practice menu) proposed in the present embodiment will be described for each kind of practice.

(1.7.3 Expression Search Learning)

An example of the expression search learning will first be described with reference to FIGS. 12 to 17. FIGS. 12 to 17 are explanatory diagrams of assistance in explaining an example of practice menus related to the expression search learning. The expression search learning is a process of performing learning related to interpretation and sensibility for a musical piece intended to be played, and is a process of searching for and determining an ideal expression through analysis of a score of the musical piece (including score reading) and trial and error. When such expression search learning is insufficient, mechanical playing lacking in expressivity may result, or improvisatorial playing with different expression may result even in a case where a same musical piece is played. In particular, learning by pursuing an expression of a desired image proceeds on the basis of the sensibility and aesthetic sense of the user (person to be instructed), can therefore be said to be one form of reinforcement learning as learning based on a reward from a viewpoint of brain science, and also affects the establishment of a skill or the like to be described later.

Figure 12:
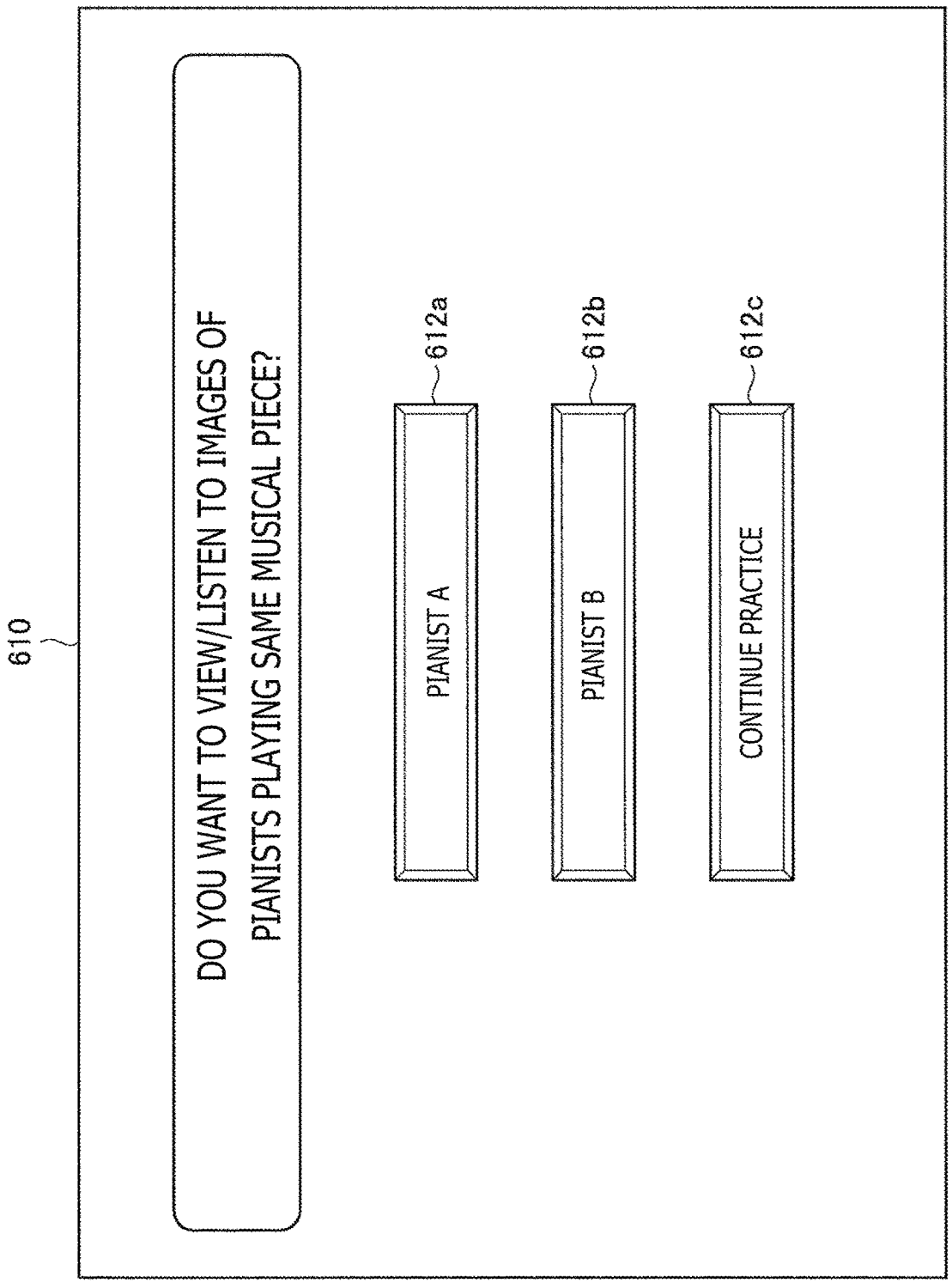
FIG. 12 is an explanatory diagram (1) of assistance in explaining an example of a practice menu for expression search learning.

In the present embodiment, the server 30 may present sound data or moving images of other players playing a same musical piece as the musical piece that the user (person to be instructed) is learning as one of practice menus assisting in the expression search learning. For example, the server 30 can present a screen display 610 as illustrated in FIG. 12 to the person to be instructed. The screen display 610 includes a plurality of buttons 612a and 612b in order to provide images of other players. The person to be instructed can view/listen to the image of another desired player by operating the button 612a or 612b. The screen display 610 may further include a button 612c for selecting continuation of practice without viewing/listening to the image of another player.

Figure 13:
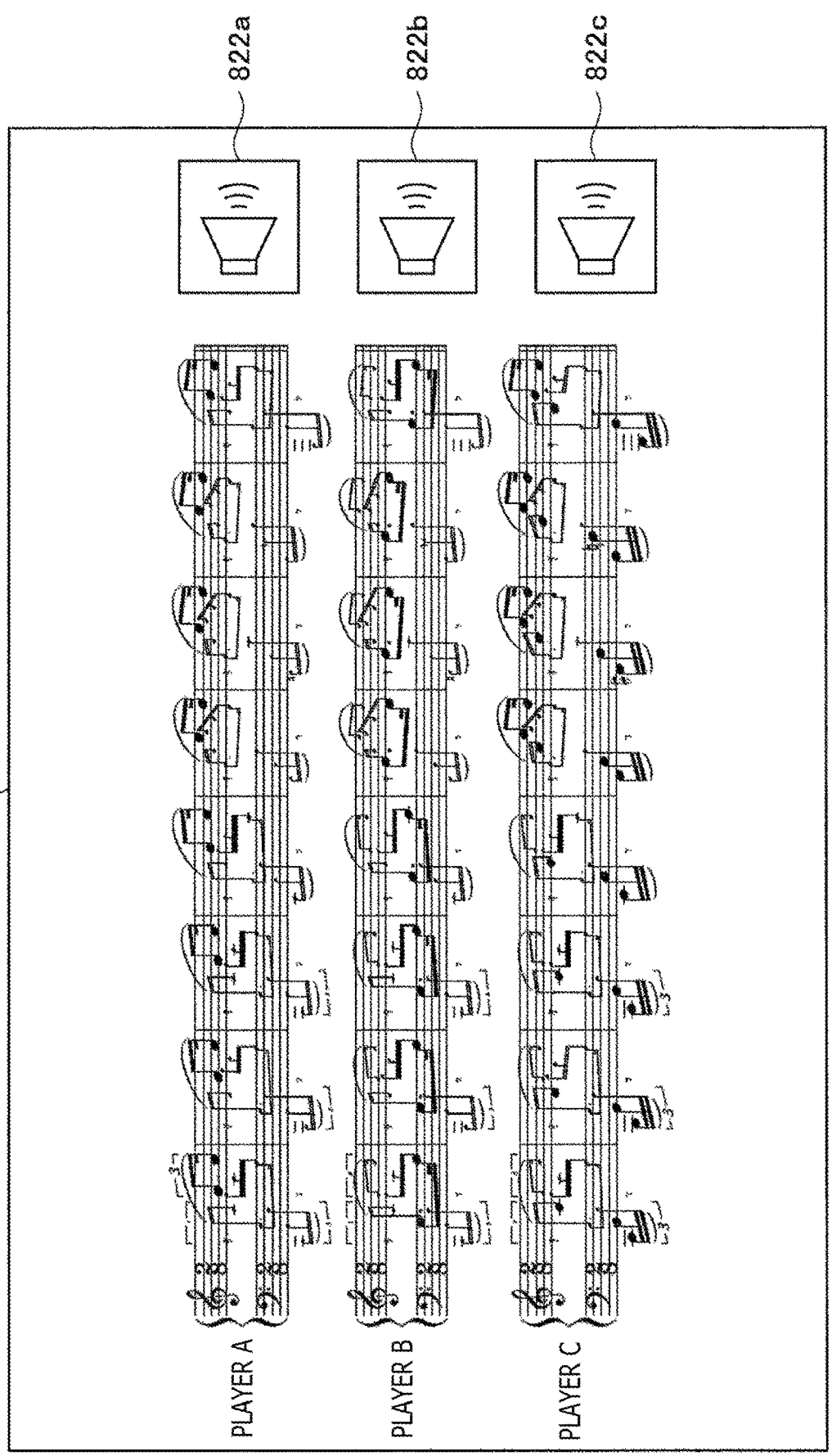
FIG. 13 is an explanatory diagram (2) of assistance in explaining an example of a practice menu for the expression search learning.

Further, in the present embodiment, the server 30 may present a screen display 820 as illustrated in FIG. 13 to the person to be instructed. The screen display 820 is a screen that provides a practice menu for learning different interpretations of a same musical piece. The screen display 820, for example, displays a plurality of scores based on a result of interpretations by different players of a beginning part of a prelude (Op. 28) composed by Chopin. Incidentally, suppose that in the scores, musical notes corresponding to sounds interpreted as main sounds are illustrated so as to be larger than other musical notes. That is, in the present embodiment, the size of musical notes on the score may be displayed so as to be changed according to the interpretations of the players. The screen display 820 further includes a plurality of buttons 822a, 822b, and 822c corresponding to the respective scores. The person to be instructed can listen to playing data corresponding to a desired interpretation by operating the button 822a, 822b, or 822c. Thus, in the present embodiment, the person to be instructed can deepen a search for the own expression by coming in touch with expressions based on the various interpretations of the same musical piece or the like.

Figure 14:
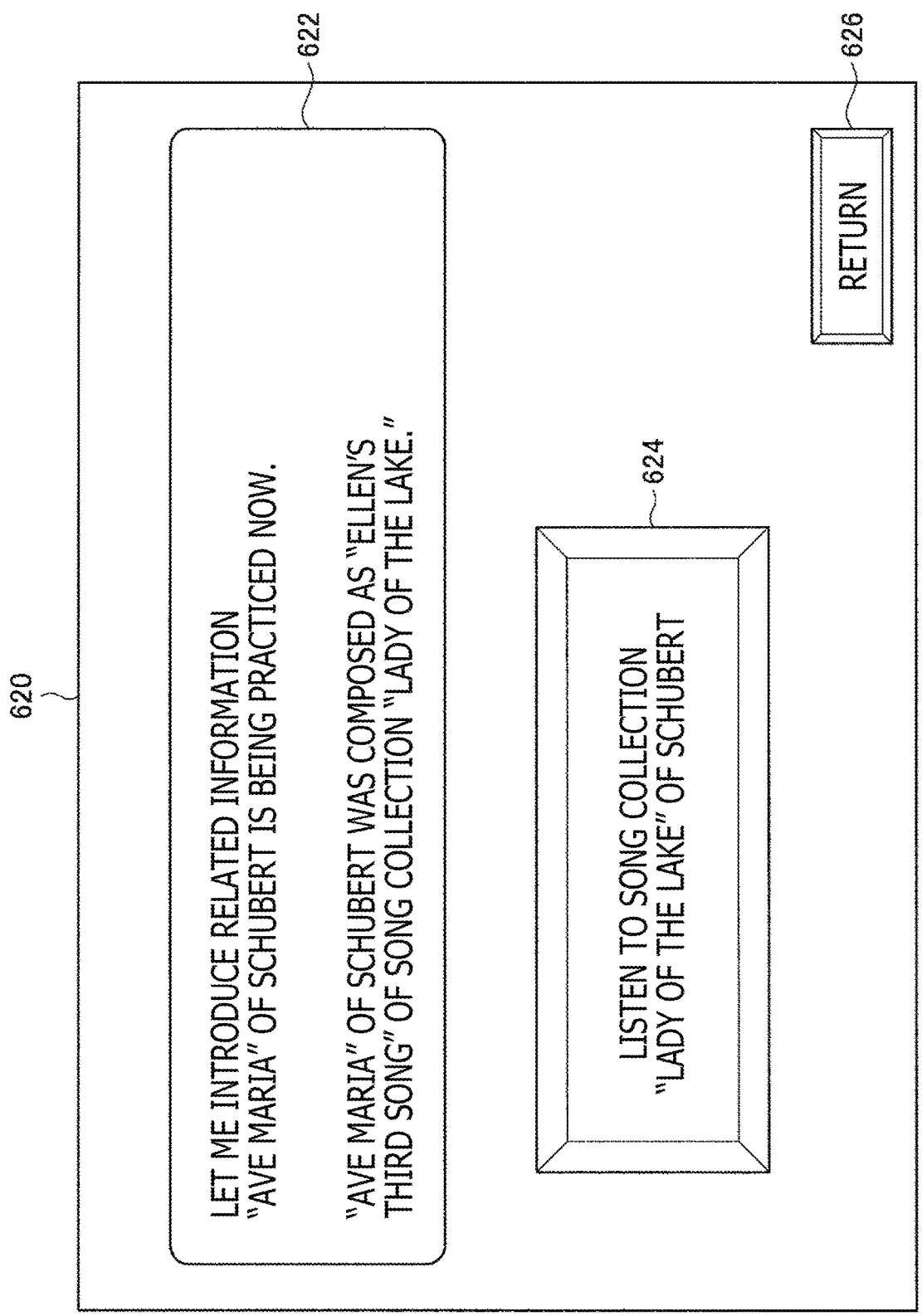
FIG. 14 is an explanatory diagram (3) of assistance in explaining an example of a practice menu for the expression search learning.

In addition, in the present embodiment, another musical piece of the composer of the musical piece that the person to be instructed is learning and another musical piece composed by a different composer and having a same phrase or a same harmonic progression as the musical piece may be presented as one of the practice menus assisting in the expression search learning. For example, the server 30 may present a screen display 620 as illustrated in FIG. 14 to the person to be instructed. In the example of FIG. 14, the person to be instructed is learning a playing method of "Ave Maria" composed by Schubert. Therefore, the screen display 620 includes a window display 622 displaying related knowledge of the musical piece, and includes a button 624 for viewing/listening to a song including the musical piece. The person to be instructed can view/listen to an image of the song by operating the button 624. The screen display 620 may further include a button 626 for selecting continuation of practice without viewing/listening to the image of the song.

Figure 15:
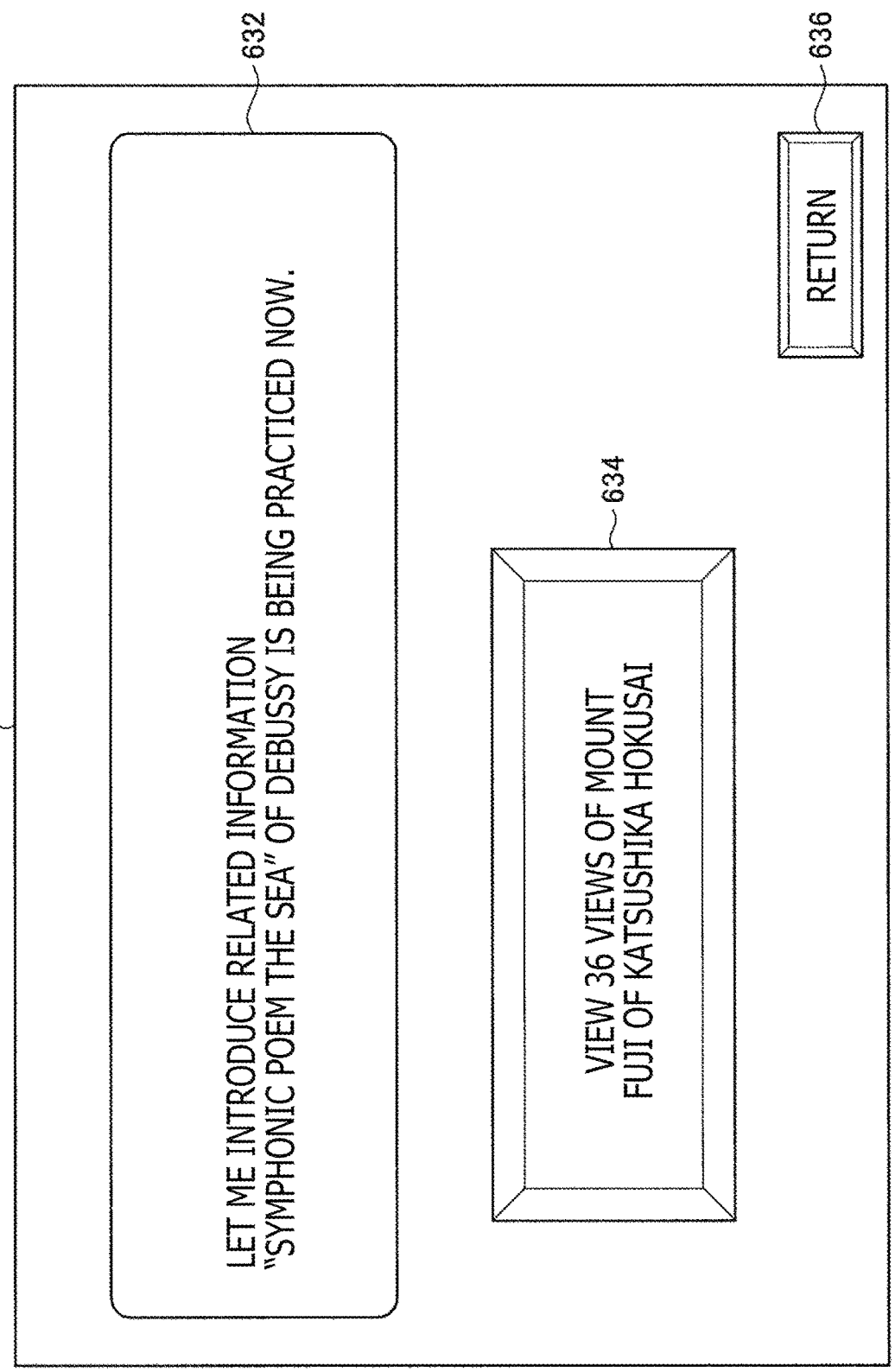
FIG. 15 is an explanatory diagram (4) of assistance in explaining an example of a practice menu for the expression search learning.

Further, is the present embodiment, related knowledge of a novel, a picture, or the like related to the musical piece that the person to be instructed is learning may be presented as one of the practice menus assisting in the expression search learning. For example, the server 30 may present a screen display 630 as illustrated in FIG. 15 to the person to be instructed. In the example of FIG. 15, the person to be instructed is learning a playing method of "symphonic poem The Sea" composed by Debussy. Therefore, the screen display 630 includes a button 634 displaying the 36 Views of Mount Fuji by Katsushika Hokusai, which have been included on the display of a first edition of a score of the musical piece, as related knowledge of the musical piece. The person to be instructed can view the pictures related to the musical piece by operating the button 634. The screen display 630 may further include a window display 632 indicating that the person to be instructed is learning the playing of "symphonic poem The Sea" composed by Debussy and a button 636 for selecting continuation of practice without viewing the pictures. Further, in the present embodiment, a biography, a letter, a note, or the like of the composer who composed the musical piece being learned may be presented as related knowledge. By learning such related knowledge, the person to be instructed can obtain a deep understanding of the musical piece.

In addition, in the present embodiment, the score of the musical piece that the person to be instructed is learning may be presented, various interpretations and arrangements (for example, harmonic progressions, rhythm structures, polyphonies, fingerings, phrases, and the like may be presented, and the person to be instructed may be made to try such arrangements. For example, the server 30 can present a screen display 640 as illustrated in FIG. 16 to the person to be instructed. The example of FIG. 16 illustrates the screen display 640 for the person to be instructed himself/herself to learn to add a chord to a musical piece That the person to be instructed is learning. The screen display 640 includes a score display 642 illustrating a part of the score of the musical piece being learned and a score display 644 displaying a chord added by the person to be instructed. The person to be instructed adds a chord to a melody displayed by the score display 642 on the application. In a case where the person to be instructed completes adding the chord to the melody, the chord added by the person co be instructed is output together with the melody. The person to be instructed can therefore confirm on the basis of sound data whether a suitable chord is added according to a rule of chord progression.

Further, in the present embodiment, morphing can be applied to the sound data of playing of the person to be instructed. By performing such morphing, the person to be instructed can deepen the expression search. As a concrete example, in the present embodiment, rhythm, articulation, a volume balance between melodies, a volume balance between a right hand and a left hand, or the like in the sound data of the playing of the person to be instructed can be changed according to an operation of the person to be instructed. In other words, in the present embodiment, an effect can be applied to the sound data of the playing of the person to be instructed. Then, by reproducing the sound data to which such an effect is applied, the person to be instructed can expand an expression search space.

Figure 17:
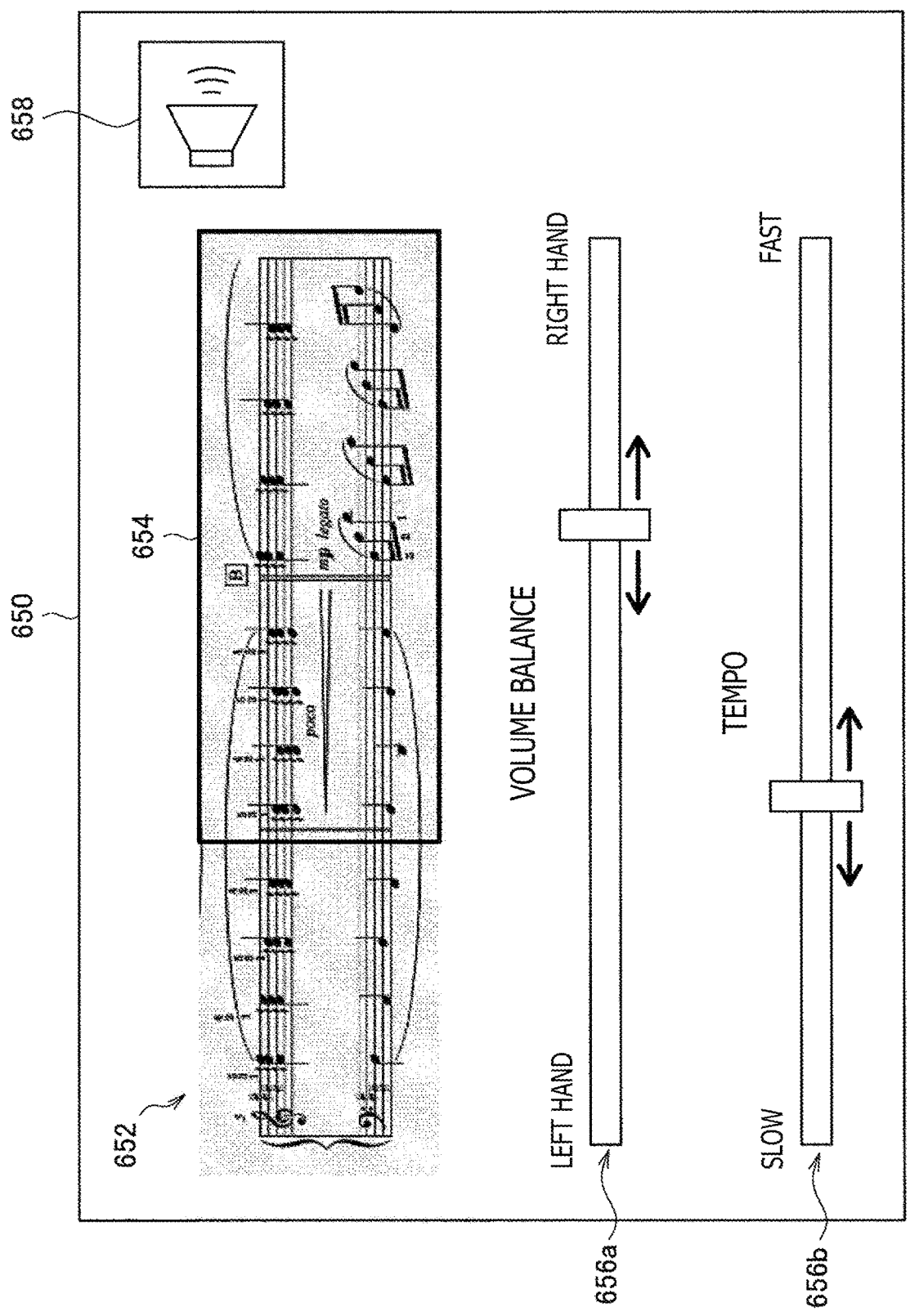
FIG. 17 is an explanatory diagram (6) of assistance in explaining an example of a practice menu for the expression search learning.

For example, the server 30 can present a screen display 650 as illustrated in FIG. 17 to the person to be instructed. In the example of FIG. 17, the screen display 650 includes a score display 652 illustrating a part of the score of a musical piece played by the person to be instructed. Further, together with a frame 654 enclosing a part of the score display 652, the screen display 650 includes a cursor 656a for changing a volume balance between the right hand and the left hand in a range enclosed by the frame and a cursor 656b for changing tempo in the range. The person to be instructed can change the volume balance and the tempo in the range enclosed within the frame by operating the cursors 656a and 656b. The screen display 650 may further include a reproduction button 658 for reproducing playing data in a range of the score illustrated by the score display 652. In addition, in the present embodiment, orchestration or the like may be performed by replacing each melody with another musical instrument.

(1.7.4 Skill Search Practice)

Figure 18:
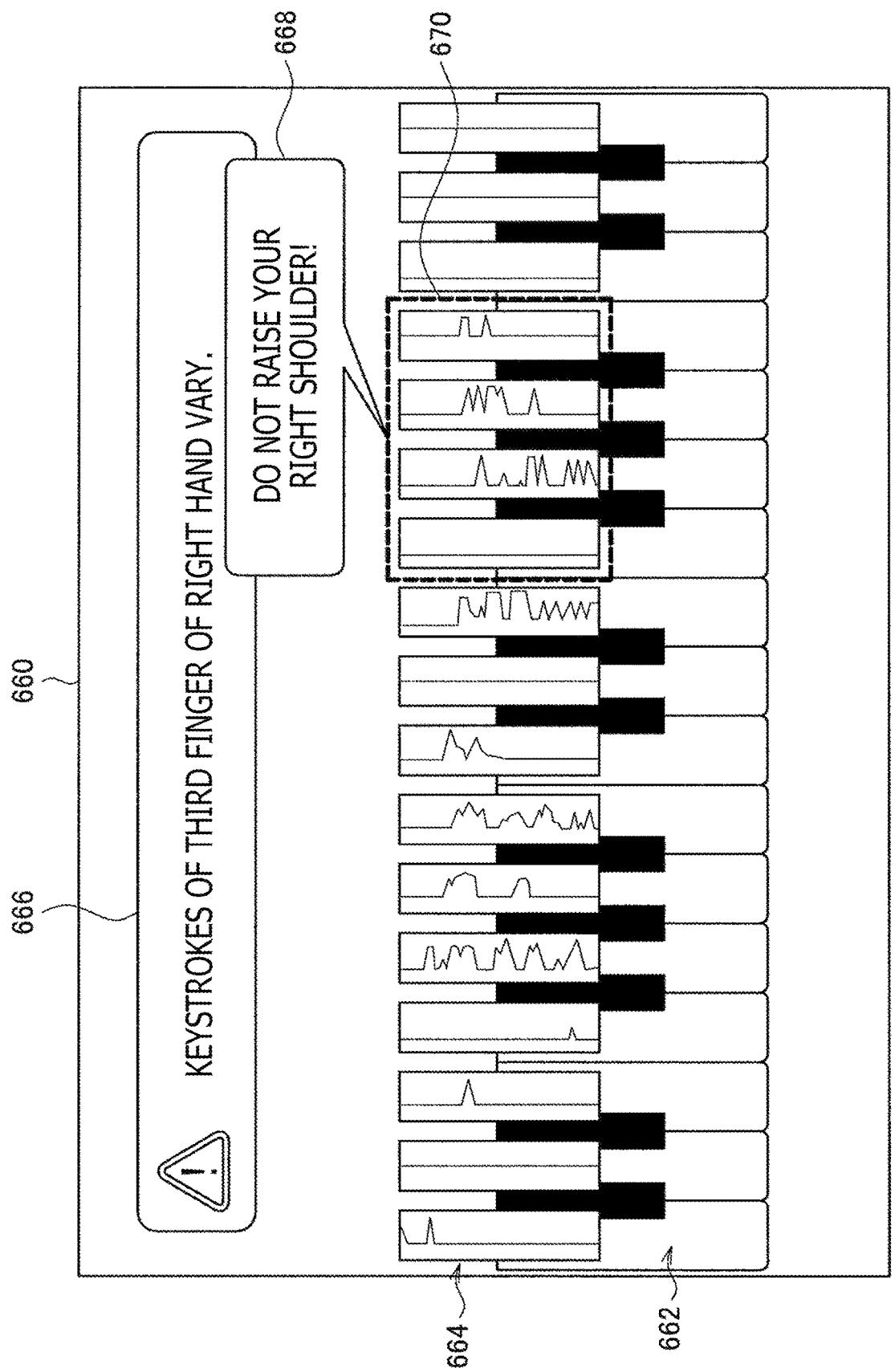
FIG. 18 is as explanatory diagram (1) of assistance in explaining an example of a screen display for a skill search practice.
Figure 19:
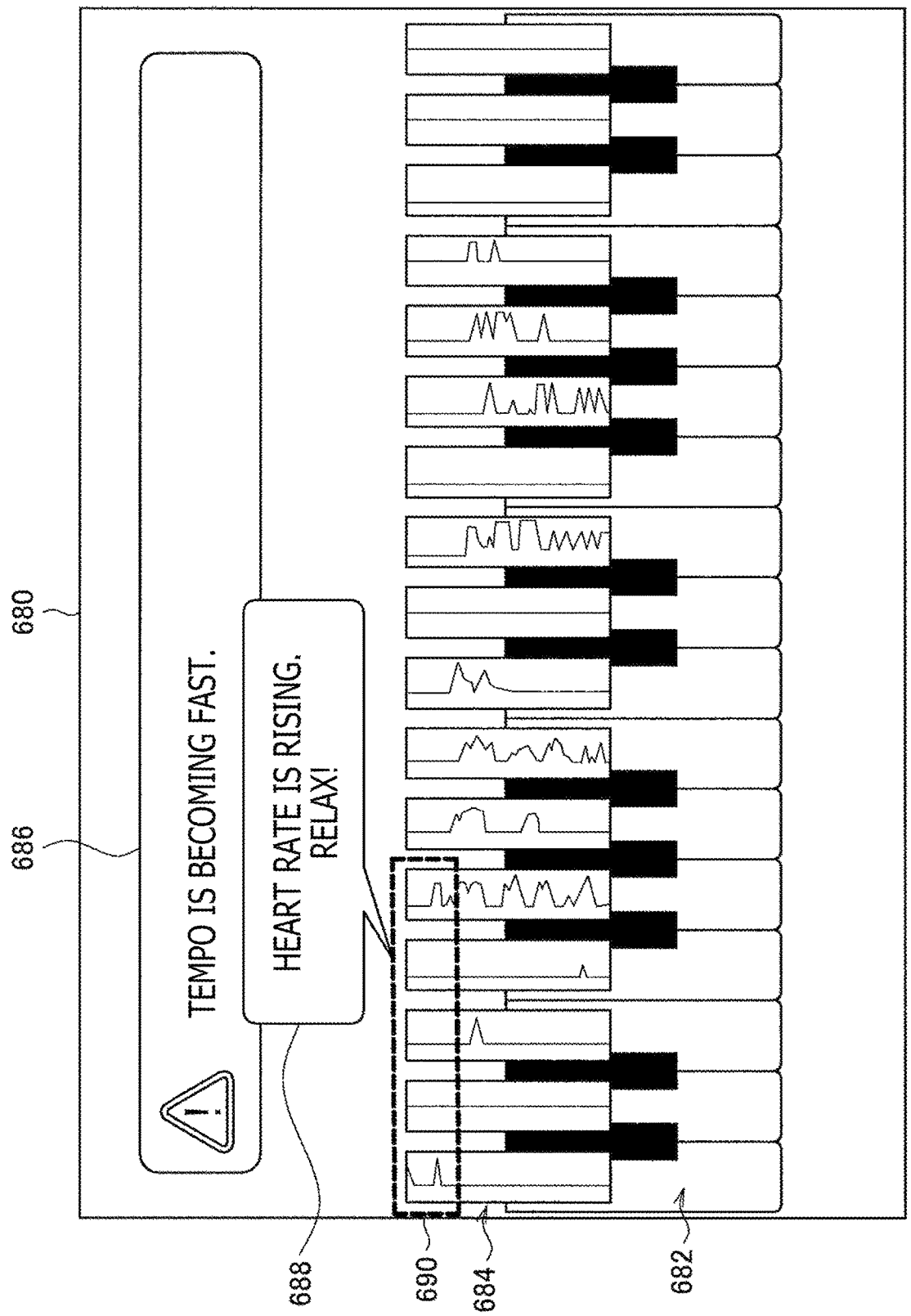
FIG. 19 is an explanatory diagram (2) of assistance in explaining an example of a screen display for the skill search practice.
Figure 20:
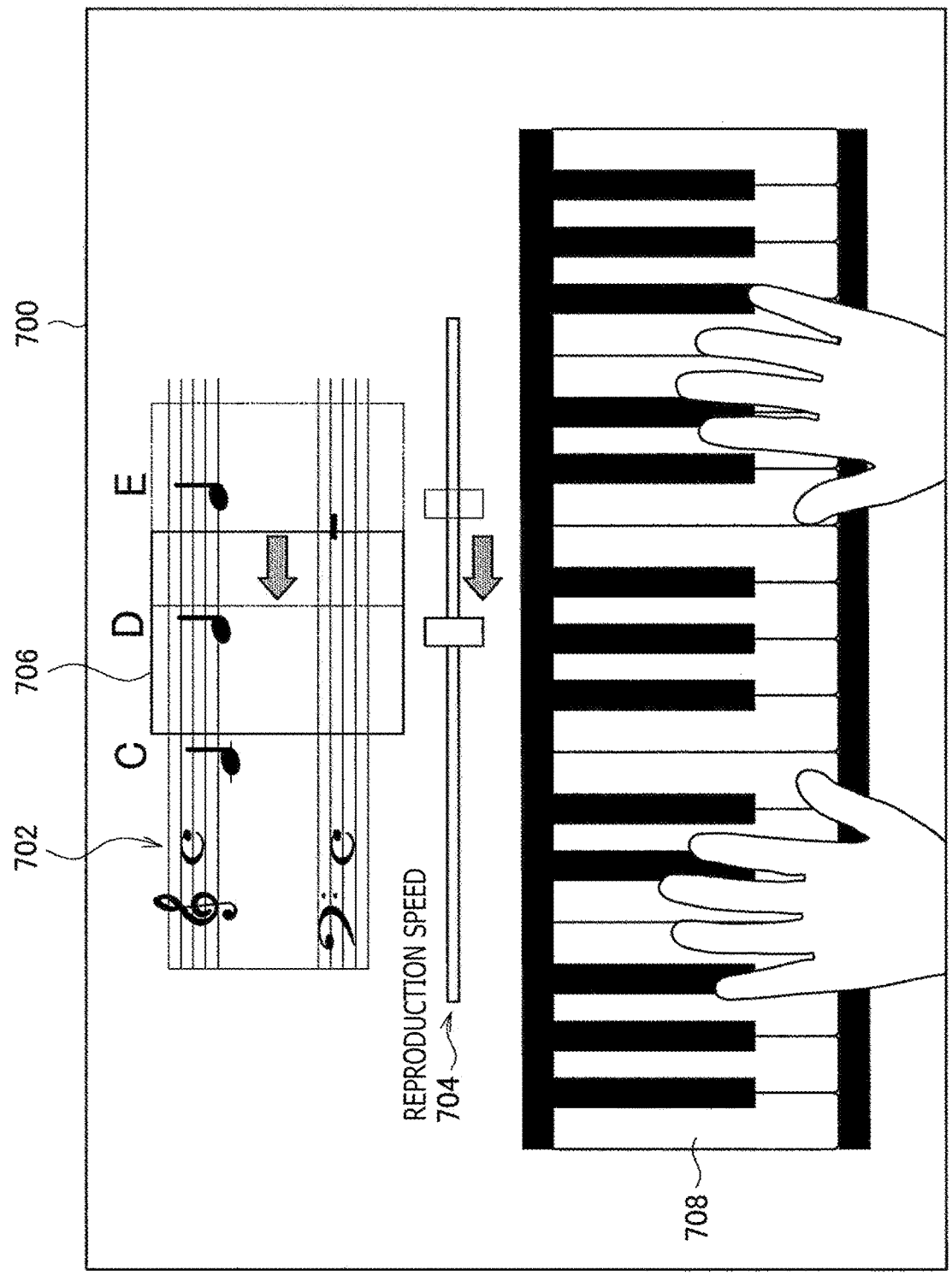
FIG. 20 is an explanatory diagram (3) of assistance in explaining an example of a screen display for the skill search practice.

An example of the skill search practice will next be described with reference to FIGS. 18 to 20. FIGS. 18 to 20 are explanatory diagrams of assistance in explaining an example of screen displays related to the skill search practice. In the present embodiment, the skill search practice is a practice process of repeating trial and error for learning a specific playing skill. Such a skill search practice can be said to be a process of making a search while performing trial and error as to a manner of usage of the body and a posture, a manner of directing attention, and a manner of using a sense (what to listen to, when to look where, or the like) to reduce an unnecessary strain on a muscle, reduce errors, and produce desired sound and expression during playing.

In the present embodiment, the server 30 analyze the learning conditions and characteristics of the skill of the person to be instructed on the basis of the sensing data or the like as information regarding up and down movements of a keyboard which up and down movements are obtained from a piano, a position at which a fingertip touches the keyboard, and a temporal change in a force applied to the keyboard. Further, as described earlier, the server 30 may numerically convert the learning conditions and characteristics of the skill which learning conditions and characteristics are obtained by analysis, and may directly present the numerically converted data to the person to be instructed. Then, the server 30 may extract a skill lacking in the user with respect to the target state on the basis of the learning conditions and characteristics of the skill which learning conditions and characteristics are obtained by the analysis, and present advice (for example, advice for form correction such as "raise your wrist higher," "do not raise your shoulder," "do not move your head back and forth," "do not hunch your back," or the like) or a practice menu (for example, a practice menu, a practice schedule, or the like for improving the skill that is lacking) to the person to be instructed on the basis of the extracted result. In addition, the presented advice or the like may be advice, homework, or the like given to the person to be instructed by the instructor during practice. The server 30 may obtain these pieces of information by having the instructor input the information, or performing voice recognition of the voice of the instructor and thereby converting the voice of the instructor into text.

In addition, as described earlier, the server 30 may analyze a temporal change in the learning conditions with respect to a skill search practice time, estimate a practice time of the skill search practice necessary for the person to be instructed to reach the target state, and present the estimated practice time. In addition, the server 30 may analyze a temporal change in a motion function with respect to the practice time of the skill search practice, for example, estimate a fatigue of a muscle or the like related to the motion function, by using the sensing data related to the motion function of the person to be instructed, and present a practice time and timing for the person to be instructed to take a break or the like according to the estimation.

Further, together with the above-described presentation, the server 30 may reproduce a moving image and playing sound of the playing of the person to be instructed. In this case, a reproduction speed thereof may be changed according to a desire of the person to be instructed. This enables the person to be instructed to check in detail a necessary part of the own playing. In addition, in the present embodiment, an animation including images corresponding to movement of the person to be instructed during the playing may be reproduced in place of the moving image. Further, the above-described presentation is not limited to presentation by a display device, but may be audio output of the advice by an audio output device, or may be biofeedback to the person to be instructed by a haptic device such as the force sense robot 50c or the like.

In the present embodiment, the server 30 may present advice by presenting a screen display 660 as illustrated in FIG. 18 to the person to be instructed in the middle of the skill search practice of the person to be instructed. For example, the screen display 660 may include window displays 666 and 668 displaying the advice to the person to be instructed together with a keyboard display 662 schematically illustrating the keyboard struck by the person to be instructed and a temporal change display 664 illustrating temporal changes in up and down movement of the keyboard by keystrokes of the person to be instructed. Further, a frame 670 illustrating the keyboard related to the advice illustrated in the window display 668 may be displayed in such a manner as to be superimposed on the keyboard display 662.

In addition, for example, the server 30 may present advice by presenting a screen display 680 as illustrated in FIG. 19 to the person to be instructed. For example, the screen display 680 may include window displays 686 and 688 displaying the advice to the person to be instructed together with a keyboard display 682 schematically illustrating the keyboard struck by the person to be instructed and a temporal change display 684 illustrating temporal changes in up and down movement of the keyboard by keystrokes of the person to be instructed. Further, a frame 690 illustrating the keyboard related to the advice illustrated in the window display 686 may be displayed in such a manner as to be superimposed on the keyboard display 682.

Further, the server 30 may, for example, present a screen display 700 as illustrated in FIG. 20 to the person to be instructed. For example, the screen display 700 includes a moving image display 706 displaying a moving image of keystrokes of the person to be instructed, and further includes a score display 702 illustrating a score including a part of a musical piece played by the person to be instructed in the moving image according to reproduction of the moving image. Further, a range in which the moving image is generated can be set by sliding a frame 706 displayed in such a manner as to be superimposed on the score display 702. Further, the reproduction speed of the moving image can be controlled by operating a cursor 704.

Thus, in the present embodiment, it is possible to effectively assist the person to be instructed in the learning of the skill by presenting not only the data (temporal changes) of a motion element related to the skill but also various kinds of advice or the like in the skill search practice. Further, the present embodiment is not limited to modes as illustrated in FIGS. 18 to 20. Information regarding a degree of mastery of each numerically converted skill may be displayed as a graph such as a circle graph, a bar graph, or the like, or numerical values themselves may be displayed in text. Further, in the present embodiment, the mastery level of the skill of the person to be instructed may be displayed in a manner of Sugoroku (board game). This makes it possible to easily recognize where the mastery level of the skill of the person to be instructed in the present situation is positioned with respect to the target state.

Further, in the present embodiment, in a case where the server 30 detects a rise in heart rate or the like due to nervousness in a practice before performing before the audience or the like, the server 30 may present advice prompting for movement for relaxation such as taking a deep breath or the like. In addition, it is said that a decrease in performance at a time of performing before the audience can be prevented by performing a practice while a state of tension in the practice is brought close to a practice state at a time of performing before the audience. Thus, conversely, in a case where the heart rate during the practice is too low, the server 30 may present advice prompting for performing practice with the heart rate brought close to that at a time of tension.

(1.7.5 Function improving Training)

An example of function improving training will next be described with reference to FIGS. 21 to 24. FIGS. 21 to 24 are explanatory diagrams of assistance in explaining an example of function improving training.

There is a case where target playing cannot be realized even when the skill search practice as described above is repeated. For example, playing rhythm becomes inaccurate because the person to be instructed cannot move fingers independently of each other, or the person to be instructed may not be able to realize the sounds of different tones because the person to be instructed cannot distinguish a difference between tones. In such a case, training for improving a motion function and a sensory function of the person to be instructed is more effective than the skill search practice.

Accordingly, the present embodiment presents "basic function improving training (stretching, muscle training, auditory function training, vision training, or the like)" to be performed apart from the musical instrument. The training presented in the present embodiment may be an existing training method (for example, a "Suzuki method," a "Mikimoto method," or the like), or may be training in a form of a game. Incidentally, in order to improve the motion function or the sensory function by such function improving training, the training is desired to be performed repetitively. Hence, in the present embodiment, motivation of the person to be instructed for performing the training is preferably enhanced by enhancing game characteristics or indicating temporal changes in the function of the person to be instructed. Further, in the present embodiment, in a case where the training has not been performed for a long period, the person to be instructed is preferably prompted to resume the training by presenting an alert to the person to be instructed.

Figure 21:
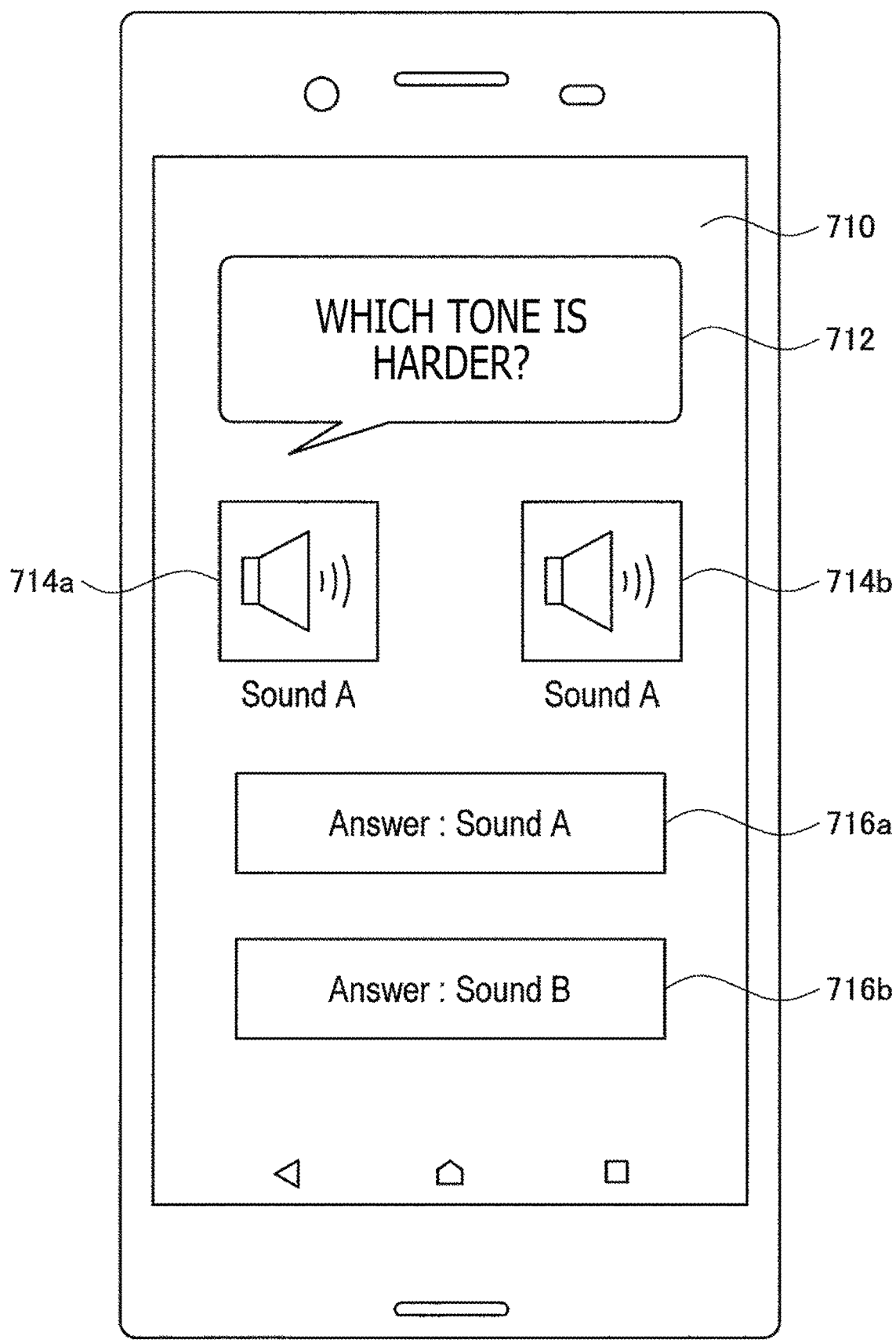
FIG. 21 is an explanatory diagram (1) of assistance in explaining an example of function improving training.

Specifically, in the present embodiment, as illustrated in FIG. 21, for example, training in which two stimuli (tones) are consecutively presented, and the person to be instructed is made to select how the person to be instructed feels which stimulus (tone) can be cited as sensory function improving training. In the present embodiment, game characteristics are enhanced by giving a reward in a case where the person to be instructed makes a correct answer, or giving a penalty in a case where the person to be instructed makes an incorrect answer. The motivation of the person to be instructed for repeating the training is thus enhanced. Further, in the present embodiment, even when the person to be instructed cannot select the correct answer from a beginning, the person to be instructed can improve the sensory function of distinguishing tones by repeating the action of listening to the two tones and recognizing the correct answer.

For example, FIG. 21 illustrates a screen display 710 for the training of distinguishing tones. The screen display 710 includes a window display 712 presenting a question to the person to be instructed, buttons 714*a* and 714*b* as targets of operation for outputting tones to be distinguished, and buttons 716*a* and 716*b* for inputting an answer to the question. The person to be instructed operates the buttons 714*a* and 714*b*, listens to the two tones, and can input the answer by operating the button 716*a* or the button 716*b*.

Figure 22:
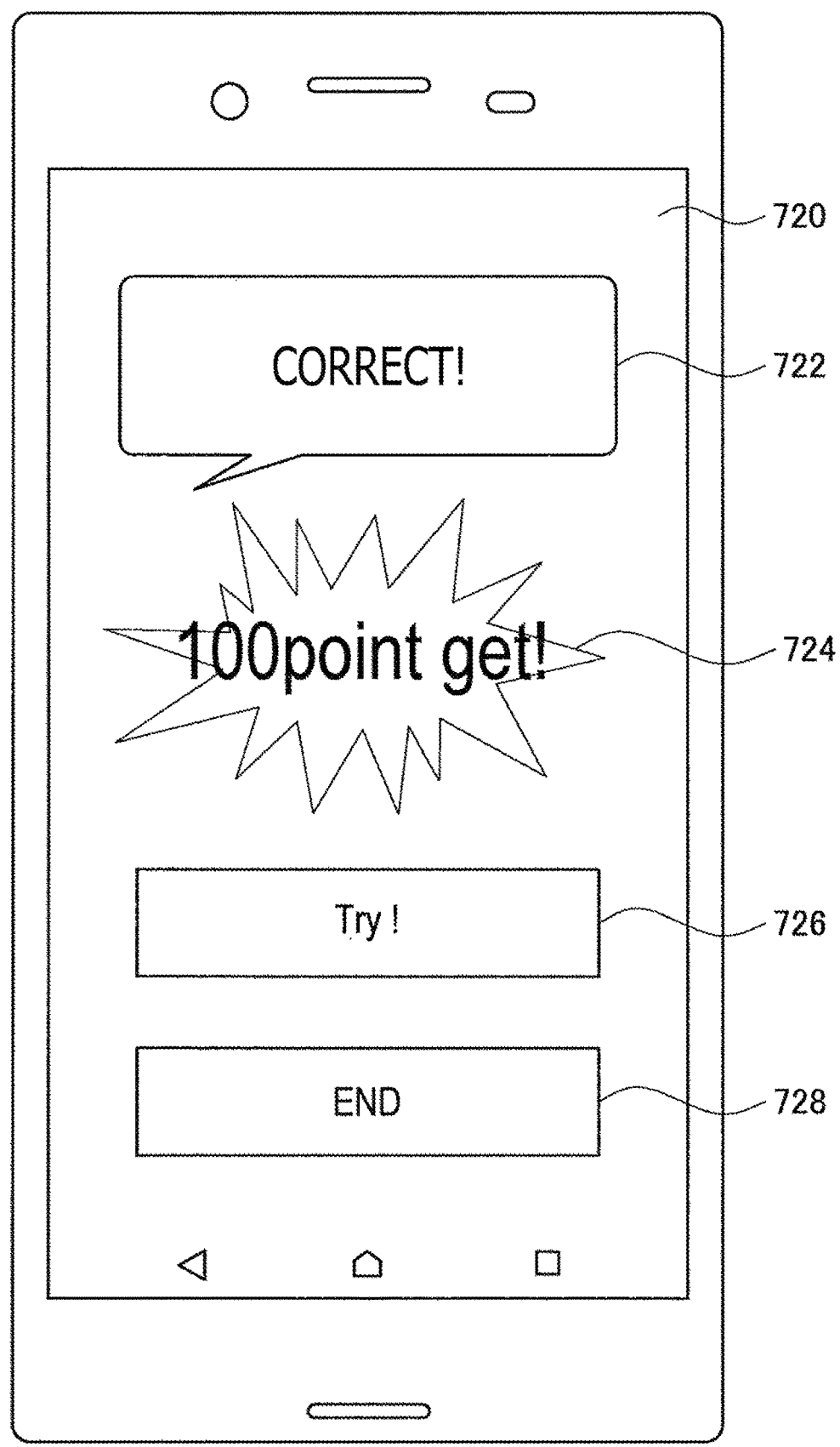
FIG. 22 is an explanatory diagram (2) of assistance in explaining an example of the function improving training.

Further, FIG. 22 illustrates an example of a screen display 720 presented in a case where the person to be instructed makes a correct answer. The screen display 720 includes a window display 722 indicating to the person to be instructed that a correct answer is made, a point display 724 indicating a reward obtained by the person to be instructed because a correct answer is made, and buttons 726 and 728 for performing input as to whether to continue the training or stop the training.

Further, in the above-described training of distinguishing the tones, the difference between the two tones may be reduced stepwise. By repeating such training, the server 30 can determine a degree of difference to which the person to be instructed can distinguish, that is, perform a threshold value evaluation of the auditory sense of the person to be instructed. In addition, in the present embodiment, a combination with a display device (not illustrated) or a haptic device such as the force sense robot 50*c* or the like enables evaluation of a perception threshold value of a visual function (example: a peripheral vision or a kinetic vision), a tactile function, and a haptic function of the person to be instructed. That is, in the present embodiment, through the training of the sensory functions, the person to be instructed can easily recognize a state of the own sensory functions, and can further recognize a strong point and a weak point of the own sensory functions by comparison with a target or the like (for example, teacher data, data of another player, or the like).

Incidentally, in the present embodiment, the sensory function improving training may be not only the training of distinguishing the hardness of the two tones but also training of distinguishing a sound volume, sounding timing, a tone, reverberation, sound quality, a chord, a rhythm, or the like. Further, in the present embodiment, as the sensory function training, a score may be presented to the person to be instructed for a predetermined time, a playing sound according to a score in a state in which the sound of only one note is removed in the same score may be next presented, and the person to be instructed may be made to make an answer as to what sound is the removed sound. According to such training, the person to be instructed can achieve not only an improvement in the sensory functions of the person to be instructed but also an improvement in a sight-reading playing skill of the person to be instructed and an improvement in a score reading ability of the person to be instructed. In addition, in the present embodiment, the sensory function training may be training such that the tone of another musical instrument is assigned to a melody of the piano, and the person to be instructed distinguishes the musical instrument. Such training makes it possible not only to improve the sensory functions but also to perform the above-described expression search learning at the same time because identical melodies by the sounds of various musical instruments can be compared with each other by listening.

Figure 23:
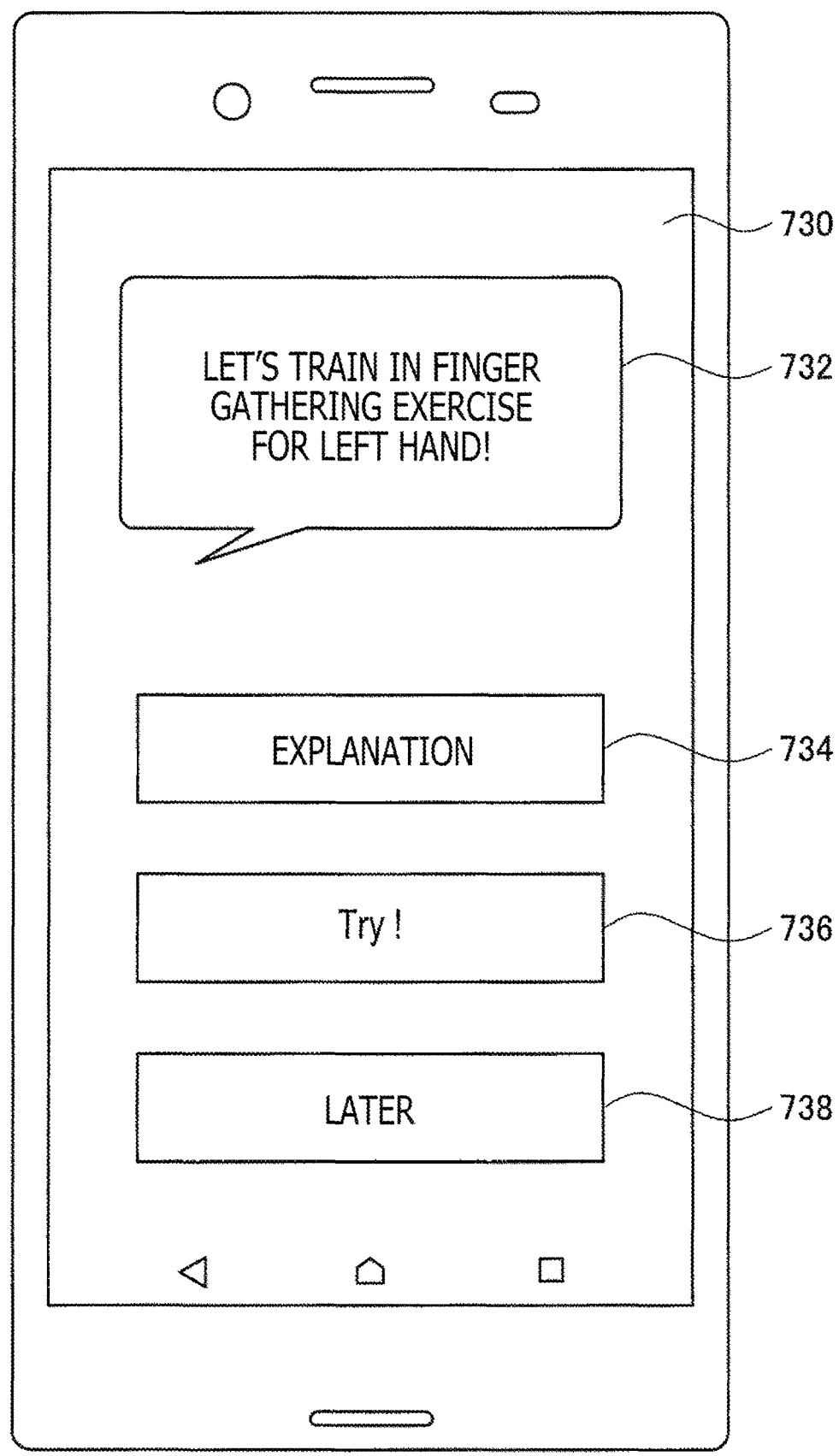
FIG. 23 is an explanatory diagram (3) of assistance in explaining an example of the function improving training.

In the present embodiment, finger exercise training as illustrated in FIG. 23, for example, may be presented as motion function improving training. For example, a screen display 730 illustrated in FIG. 23 is a screen that presents, to the person to be instructed, the training of finger gathering exercise as one kind of training that improves independence of finger motion. Incidentally, the finger gathering exercise is an exercise of sequentially repeating the following from a thumb to a little finger. All of fingers adjacent to each other are first set in a state of being in contact with each other, an interval between a thumb and an index finger is next widened and the thumb and the index finger are set in a state of being in contact with each other, and next an interval between the index finger and a middle finger is widened and the index finger and the middle finger are set in a state of being in contact with each other. It is said that the independence of finger motion can be improved by performing such an exercise rapidly.

More specifically, the screen display 730 illustrated in FIG. 23 includes a window display 732 including words that prompt the person to be instructed for the training of the finger gathering exercise, a button 734 for selecting a mode of presenting a moving image of a method of the exercise or the like and explaining the method of the exercise, and a button 736 for starting the training. Further, the screen display 730 may include a button 738 for the person to be instructed to select a mode in which the exercise is not performed. Incidentally, at a time of performing such training, the person to be instructed preferably wears sensor devices 10 such as the fingerstall type sensor device 10e or the like on fingertips. Thus, the server 30 can detect whether the fingers of the person to be instructed are moving correctly, and detect moving speeds of the fingers.

Incidentally, in the present embodiment, the motion function improving training may be not only the training of the above-described finger gathering exercise but also, for example, training such that the force sense robot 50c presents a movement, and the person to be instructed reproduces the presented movement accurately and rapidly. In addition, in the present embodiment, the motion function improving training may be training in a form of a game such that forces are exerted between a plurality of fingers with different magnitudes and timings. Further, in the present embodiment, the motion function improving training may be training such that while a predetermined finger is made to exert a force, another finger is stretched (for example, extending a third finger while trying to bend the middle finger). In particular, as for fingers, when attention is directed to the movement of a certain finger, another finger tends to be also moved according to the movement. In piano playing, it is generally preferable to suppress such a tendency and be able to move each finger freely and independently. Accordingly, in the present embodiment, the training that improves the independence of fingers as described above is preferably presented as the training of the motion function for piano playing.

Further, in the present embodiment, the game characteristics of the training may be enhanced by detecting the speed and accuracy of motion by a sensor device 10 fitted to the body of the person to be instructed at a time of the motion function improving training, and numerically converting the speed and accuracy of the motion. According to the present embodiment, this can enhance the motivation of the person to be instructed for performing the motion function improving training. In addition, in the present embodiment, exercise levels of the training of improving the sensory function and the motion function may be set stepwise, and in a case where a predetermined level is cleared, training at a suitable exercise level may be proposed next. In addition, in the present embodiment, the function improving training can be provided as a game because the function improving training can be performed even when the musical instrument is not at hand, and the person to be instructed can improve the functions while enjoying the above-described training as an entertainment.

In addition, in the present embodiment, the server 30 may present ranking in the function improving training in order to enhance the motivation of the person to be instructed more. As described earlier, at a time of the function improving training, the present embodiment can obtain a correct answer ratio of the person to be instructed, or detect and numerically convert the speed accuracy of motion by the sensor device 10 fitted to the body of the person to be instructed. Thus, ranking in the function improving training of each player can be generated and presented. Incidentally, in the present embodiment, the ranking may be generated by years of piano experience of players, by age, or by gender. Further, the present embodiment may not only generate the ranking in the function improving training, but also numerically convert the learning conditions in the above-described skill search practice and generate ranking. In such a case, the ranking may be generated by musical piece or by composer or the like.

More specifically, the server 30 can present a screen display 740 as illustrated in FIG. 24. The screen display 740 includes a ranking display 742 indicating the ranking and points of each player and a window display 744 indicating a position in the ranking and points of the person to be instructed. The present embodiment can enhance the motivation of the person to be instructed for performing the training by presenting such ranking.

(1.7.6 Practice for Establishment in Memory)

As described earlier, in a case where the person to be instructed can learn a skill that can realize a desired expression, the learned skill or toe like is desired to be established in the brain, nerves, and body of the person to be instructed. For this purpose, the skill for the desired expression is generally practiced repetitively. However, it does not suffice simply to perform the repetitive practice. By performing the repetitive practice according to a suitable schedule, it is possible to realize efficient establishment while avoiding an injury. In addition, as described earlier, performing the repetitive practice more than necessary causes an accumulation of fatigue and a decrease in motivation. Therefore, performing the repetitive practice more than necessary can be a factor in impeding efficient establishment. Further, performing the repetitive practice more than necessary may not only be as impeding factor, but also be a cause of an injury such as injury to fingers of the person to be instructed or the like in some cases.

Figure 25:
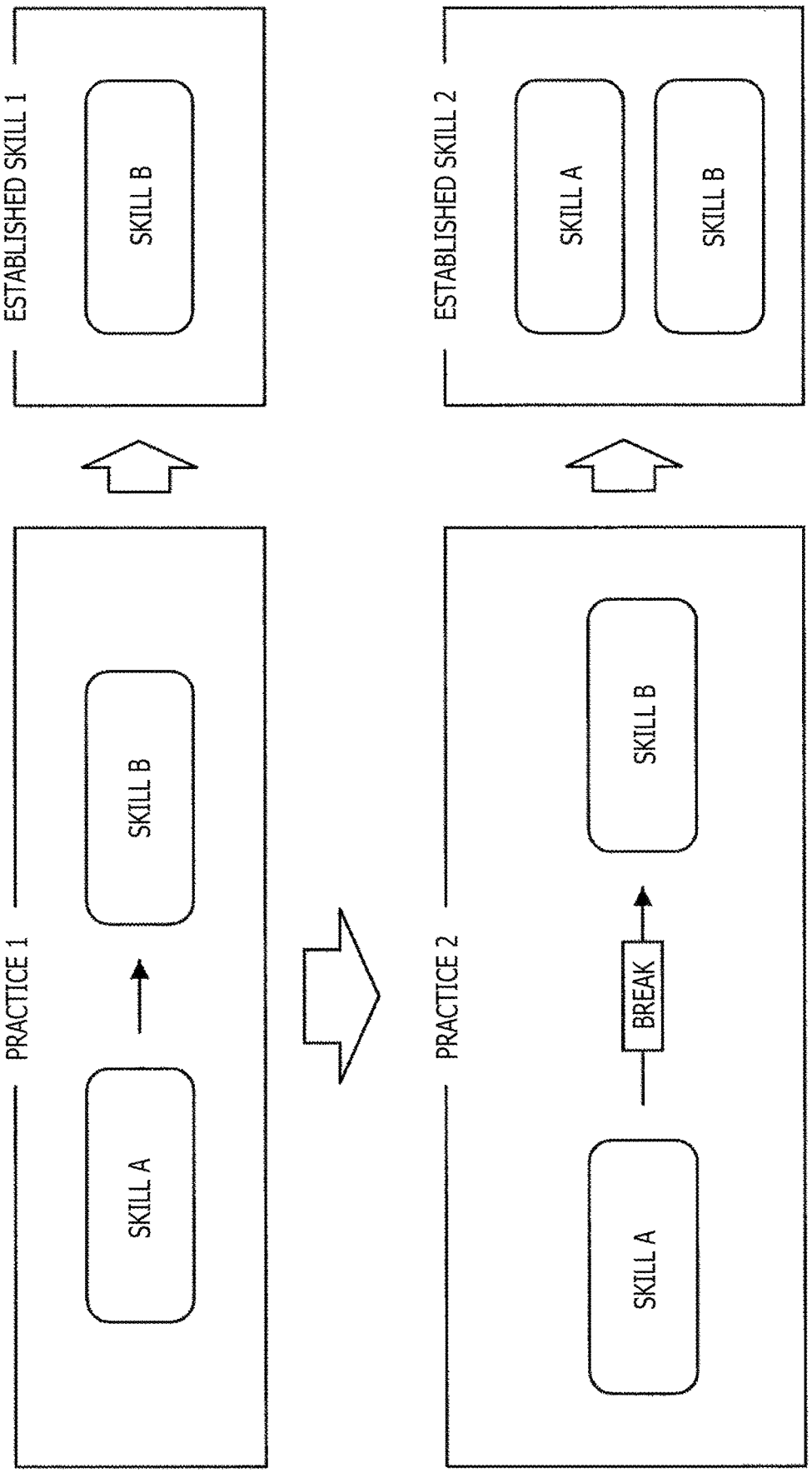
FIG. 25 is an explanatory diagram (1) of assistance in explaining an example of a practice for establishment in memory.
Figure 26:
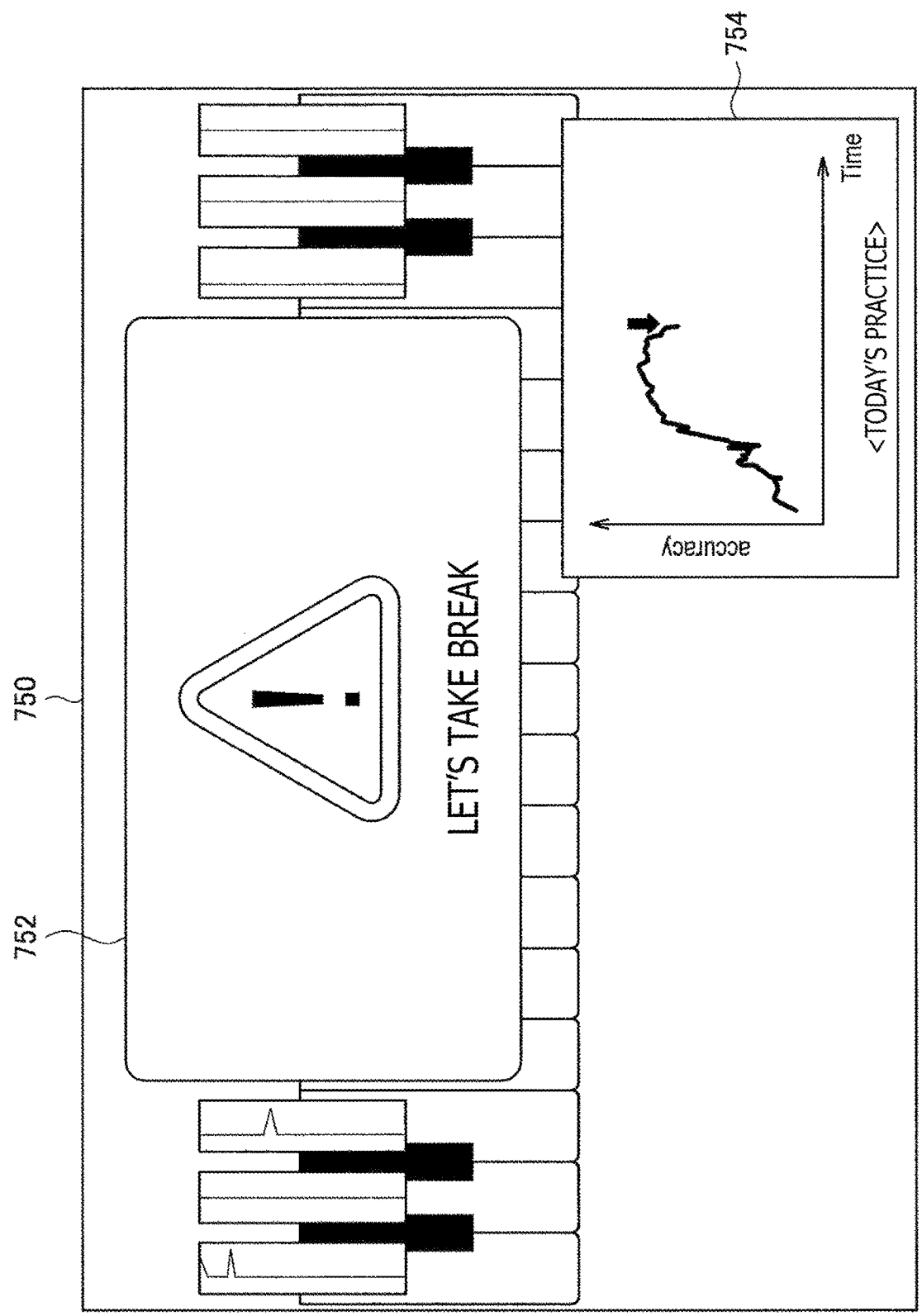
FIG. 26 is an explanatory diagram (2) of assistance in explaining an example of the practice for establishment in memory.
Figure 27:
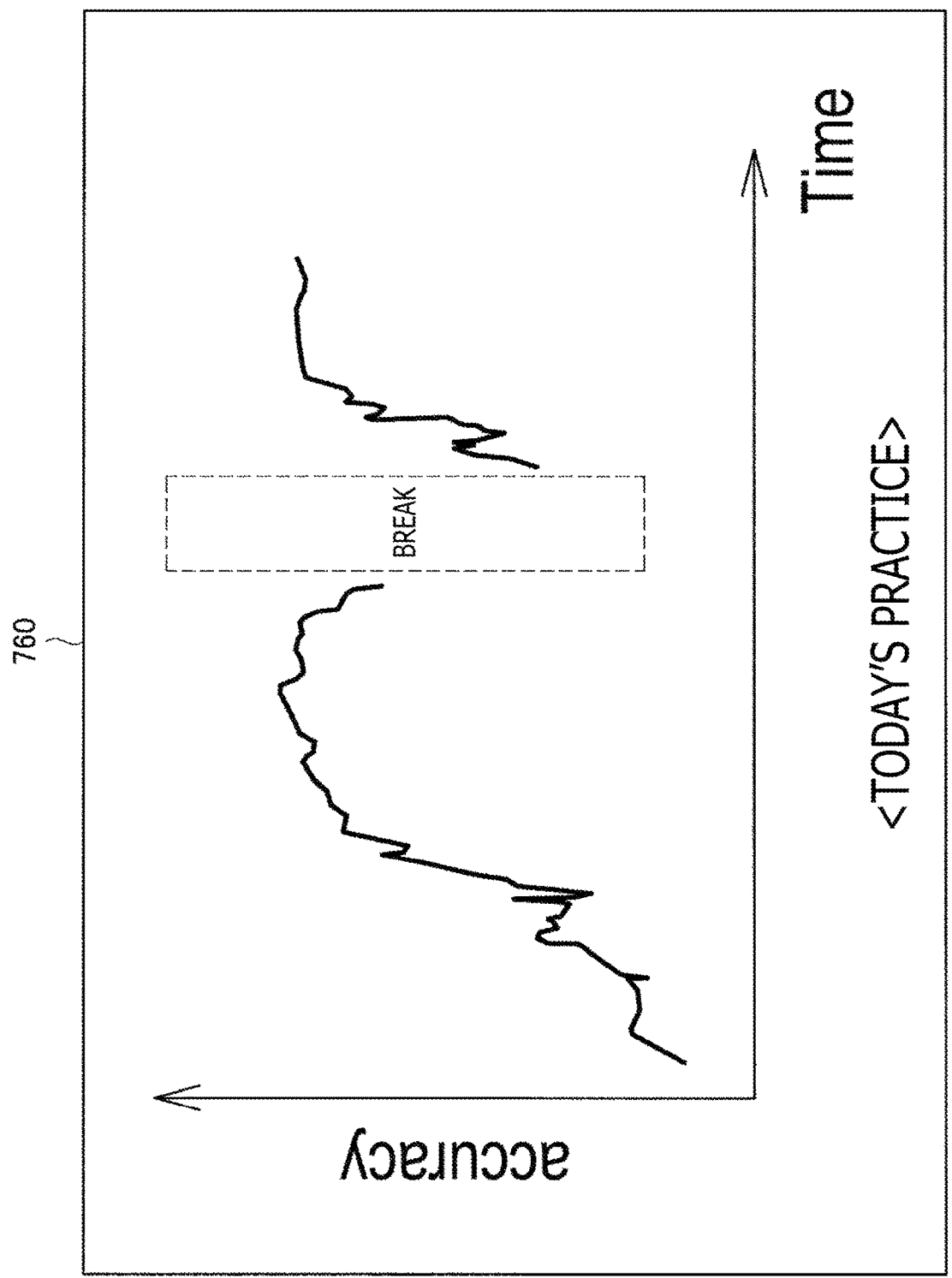
FIG. 27 is an explanatory diagram (3) of assistance in explaining an example of the practice for establishment in memory.

Accordingly, for efficient establishment, the present embodiment presents, to the person to be instructed, a suitable practice schedule as to when a practice is to be performed, how long a break is to be taken between practices, and the like. In the following, an example of practice for establishment in memory will be described with reference to FIGS. 25 to 27. FIGS. 25 to 27 are explanatory diagrams of assistance in explaining an example of practice for establishment in memory.

A method of taking a break is cited as one important element in establishment in memory. It is often that when repetitive practices of a plurality of skills are performed in order to attempt to establish the plurality of skills, the skills interfere with each other, and only one skill is established. For example, as illustrated in an upper part of FIG. 25, when a skill A and a skill B are practiced consecutively with similar amounts of practice (suppose, for example, that the skill A and the skill B are skills for playing different melodies), the establishment of the skill B may impede the establishment of the skill A, and consequently only the skill B may be established. In addition, in a case where the amount of practice of the skill A is larger than the amount of practice of the skill B, when the skill A and the skill B are practiced consecutively, only the skill A is established, and the skill B is not established.

On the other hand, as illustrated in a lower part of FIG. 25, in a case where a break of 3 to 6 hours is inserted after the practice of the skill A, and then the skill B is practiced, both of the skill A and the skill B are consequently established. This is said to be because when the break is taken, the memory of the skill A makes a transition from a short term memory to a long term memory. Hence, in a case where it is necessary to establish skills for playing many musical pieces, or in a case where methods of playing different musical pieces are to be established at the same time in order to maintain motivation for practice, it is important to perform suitable practice scheduling as to what practice is to be performed to what extent, and how long a break is to be inserted.

Hence, in the present embodiment, the server 30 may analyze the practice time and the learning conditions of each skill, determine and present an allocation of practice times such that each skill continues to be practiced in a well-balanced manner in the future, and present a suitable break time to be taken between the practice times of respective skills. Further, in the present embodiment, the server 30 may refer to the accuracy and speed of motion by analyzing various kinds of sensing data obtained by the sensor devices 10, and may estimate a degree of establishment in the person to be instructed, or estimate and present a practice time necessary for the person to be instructed to establish a skill. Specifically, for example, the server 30 plots temporal changes in numerically converted establishment conditions (for example, a keystroke accuracy, reproducibility, or the like) with respect to a practice time, performs regression analysis, and thereby analyzes a tendency of the temporal changes in the establishment conditions. Further, the server 30 may estimate a practice time necessary to attain the establishment by performing extrapolation using the obtained tendency. It is to be noted that in the present embodiment, the server 30 is not limited to performing the estimation by the method as described above, but may, for example, analyze the tendency using the above-described machine learning, and perform the estimation on the basis of a result of the analysis.

In addition, in the present embodiment, the server 30 may analyze various kinds of sensing data, and estimate a degree of fatigue of the person to be instructed. For example, temporal changes in a characteristic (for example, quickness or the like) regarding the movement of a part of the body of the player can be obtained by analyzing the sensing data. Further, from such temporal changes, the server 30 can estimate a degree of fatigue of muscle fibers of the body of the person to be instructed or the like by detecting a point in time that improvements cease to be observed or a point in time that a decrease is observed. Then, in the present embodiment, in order to avoid an accumulation of fatigue more than necessary and a decrease in motivation, the server 30 preferably make such presentation as to propose a break to the person to be instructed and present a break time for suitably eliminating the fatigue in a case where the fatigue is estimated to be equal to or more than a predetermined threshold value.

For example, the server 30 may propose a break to the person to be instructed who continues a practice for a long time by presenting a screen display 750 as illustrated in FIG. 26 to the person to be instructed. For example, the screen display 750 may include a window display 752 displaying words prompting for a break and a temporal change display 754 indicating temporal changes in a skill that the person to be instructed aims to establish. Making such a screen display 750 can prompt the person to be instructed for a break, and make the person to be instructed feel more convinced of the proposition of a break by indicating that a fatigue is observed because there is a decline in the skill. According to the present embodiment, the establishment can be performed more effectively when such a screen display 750 is made. Further, according to the present embodiment, it is possible to avoid a risk of fatigue or injury due to a practice for a long time or the like.

Further, in the present embodiment, the server 30 may explicitly indicate an effect of taking a break by presenting a screen display 760 as illustrated in FIG. 27 to the person to be instructed. The screen display 760 illustrates temporal changes in the skill that the person to be instructed aims to establish, and enables easy recognizing of how the skill changes when a break is inserted. Further, a time of the break to be taken by the person to be instructed is also indicated in the temporal changes. In the present embodiment, the person to be instructed can recognize the importance of a break by viewing such temporal changes, and can be prompted to take a break according to the proposition of the server 30. Further, by referring to a study log stored in the server 30 together with such temporal changes, the person to be instructed can easily realize what kind of skill or the like has been improved by what practice, and is also provided with a material for considering a better practice menu.

<1.8. Example of Presentation>

Figure 28:
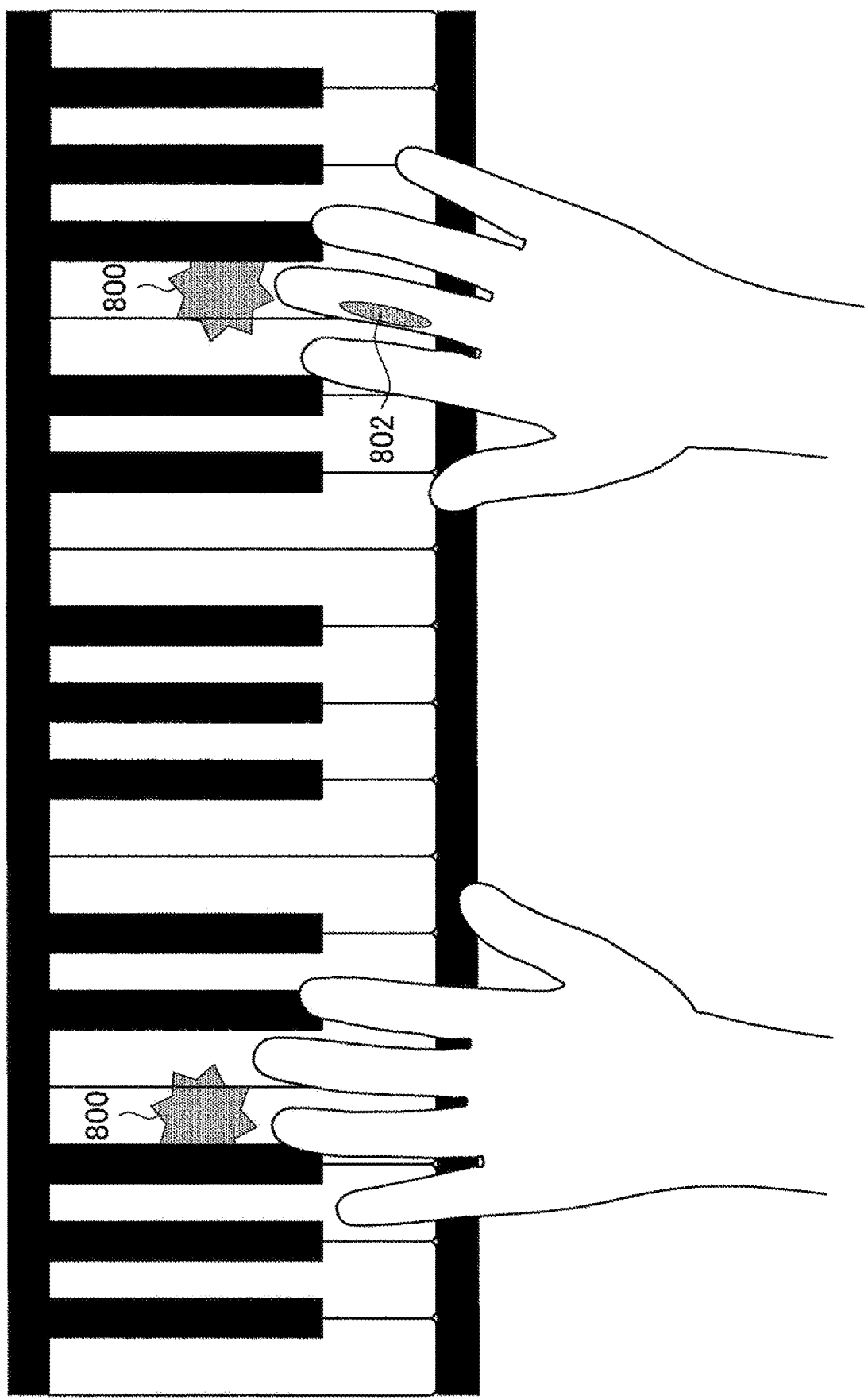
FIG. 28 is an explanatory diagram (1) of assistance in explaining an example of presentation according to the same embodiment.
Figure 29:
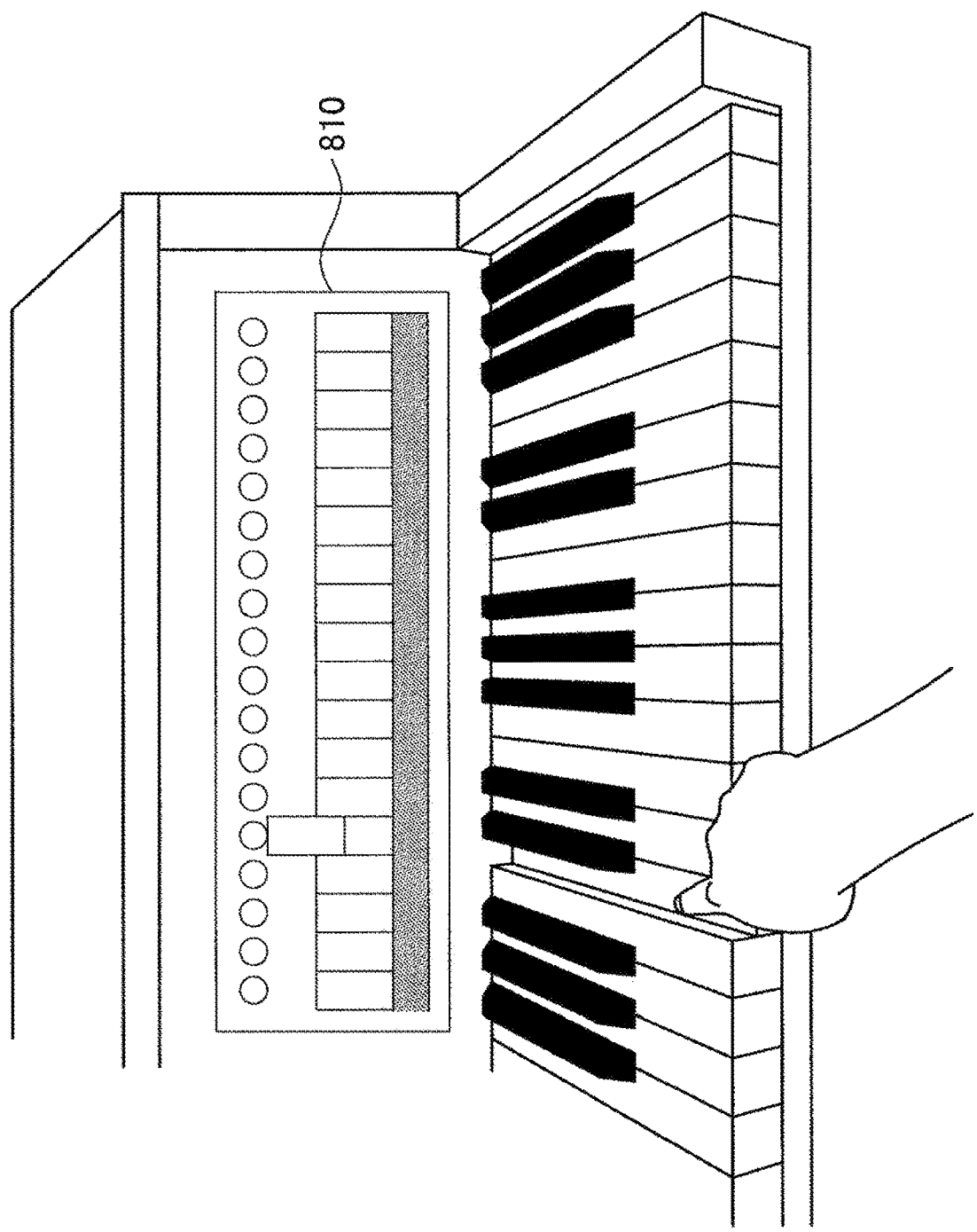
FIG. 29 is an explanatory diagram (2) of assistance in explaining an example of presentation according to the same embodiment.
Figure 30:
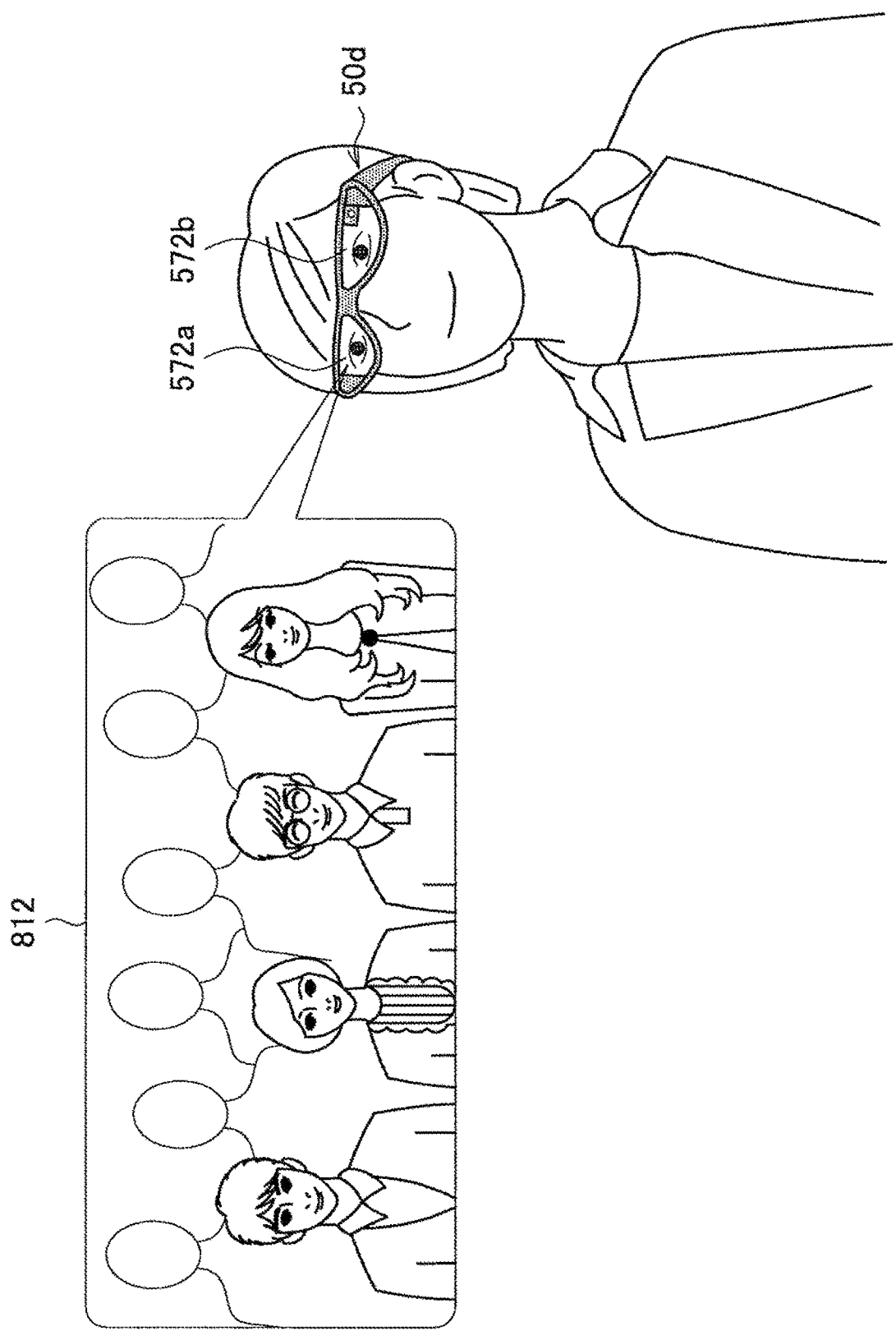
FIG. 30 is an explanatory diagram (3) of assistance in explaining an example of presentation according to the same embodiment.

An example of presentation according to the present embodiment will next be described with reference to FIGS. 28 to 30. FIGS. 28 to 30 are explanatory diagrams of assistance in explaining an example of presentation according to the present embodiment. In the present embodiment, as described thus far, various means and forms can be used for presentation to the person to be instructed. Further, presentation using the smart glasses 50*d* will be described as an example of presentation according to the present embodiment.

Specifically, in the present embodiment, with the use of the smart glasses 50*d*, various kinds of information based on various kinds of sensing data can be displayed as virtual objects in such a manner as to be superimposed on an object or the like in a real space, for example, on the body of the person to be instructed or a musical instrument such as a piano or the like. More specifically, as illustrated in FIG. 28, for example, markers 800 indicating information such as positions at which fingertips of the person to be instructed strike a keyboard and keyboard accelerations can be displayed in such a manner as to be superimposed on the keyboard of a piano. In addition, for example, a marker 802 having a shade of color reflecting information such as a finger acceleration or an amount or muscle activity may be displayed so as to appear on a finer of the person to be instructed. In addition, in a case of, for example, a violin or the like rather than the piano, a position at which a finger of the person to be instructed presses a string, a speed or an acceleration at which a bow rubs the string, and a contact position between the string and the bow may be displayed in such a manner as to be superimposed on the string. Thus, according to the present embodiment, "visualization" of information normally not visible to the eyes facilitates clear recognition of a tendency or a problem in the playing of the person to be instructed himself/herself.

Further, in the present embodiment, an internal state of the musical instrument may be virtually visualized by using the smart glasses 50*d*. Incidentally, a part of players (professional pianists in particular) are said to learn a subtle feeling such as a touch on the keyboard or the like by performing training while imagining movements of an action mechanism including hammers that transmit movements of the keyboard to strings. However, in the case of the piano, for example, whereas movements of a front half of the keyboard can be visually recognized directly because the front half of the keyboard is exposed to the outside of the piano, movements of a rear half of the keyboard cannot be visually recognized because the rear half of the keyboard is located within the piano. Further, the movements of the above-described action mechanism cannot be visually recognized because the action mechanism is also similarly located within the piano.

Accordingly, in the present embodiment, an imaging device (not illustrated) is installed within the piano, the movements of the above-described action mechanism are imaged, and a moving image of the imaged action mechanism is displayed in such a manner as to be superimposed on the front of the piano in real time by using the smart glasses 50*d*. Alternatively, in the present embodiment, a sensor device 10 that detects the movements of the above-described action mechanism may be installed for the mechanism within the piano, and the movements detected by the sensor device 10 may be converted into an animation. In this case, as illustrated in FIG. 29, the animation 810 is displayed in such a manner as to be superimposed on the front of the piano by using the smart glasses 50*d*. Further, in the present embodiment, the server 30 may estimate the movements of the above-described action mechanism from sensing data regarding the movements of the keyboard which sensing data is obtained by the sensor section 100 such as a pressure sensor or the like, convert the estimated movements into an animation, and display the animation in a superimposed manner.

In the present embodiment, the movements of the action mechanism within the piano, which movements are usually not visible to the eyes, are "visualized" by various kinds of virtual objects. Thus, the person to be instructed can perform a practice while conscious of the movements of the action mechanism. Hence, according to the present embodiment, it is possible to provide a practice effective in learning a subtle feeling such as a touch on the keyboard or the like.

Further, in the present embodiment, as illustrated in FIG. 30, images of an audience, judges, and a concert hall may be virtually displayed in a superimposed manner by using the smart glasses 50*d*, Specifically, in the present embodiment, it is preferable to detect the angle of a head portion of the person to be instructed by a motion sensor (not illustrated) fitted to the smart glasses 50*d* or the like in a case where the person to be instructed plays a piano, display the image of the audience according to the angle (for example, in a case where it is detected that the head portion of the person to be instructed is facing in the direction of an auditorium), and display the image in a changing manner. Further, in the present embodiment, the sound of the piano played by the person to be instructed may be collected as sensing data, and the displayed image of the audience may be changed according to a change in the sensing data. This can provide the person to be instructed with a sense of realism. Hence, according to the present embodiment, by performing practice while conscious of the audience and the judges that are not actually present in front of the person to be instructed, the person to be instructed can virtually experience a situation such as a situation of performing before the audience, that is, a situation of playing before the audience or the like in a hall. According to the present embodiment, this enables a player to perform training against "stage fright," which is nervousness more than necessary when the player plays before the audience or the like.

2. Summary

As described above, the foregoing embodiment of the present disclosure can provide an information processing device, an information processing method, and a program that can effectively assist in performance learning. More specifically, according to the embodiment of the present disclosure, the user can be provided with, for example, a suitable practice menu, a practice time, a break, advice, and the like in a suitable sense modality (a visual sense, an auditory sense, a tactile sense, or the like) and a suitable format (a game format, a ranking format, or the like). Thus, the user can be effectively assisted n performance learning. Incidentally, the information processing platform 1 according to the embodiment of the present disclosure can be used in such a manner as to be integrated with another system, a device, a sensor, or the like.

3. Hardware Configuration

Figure 31:
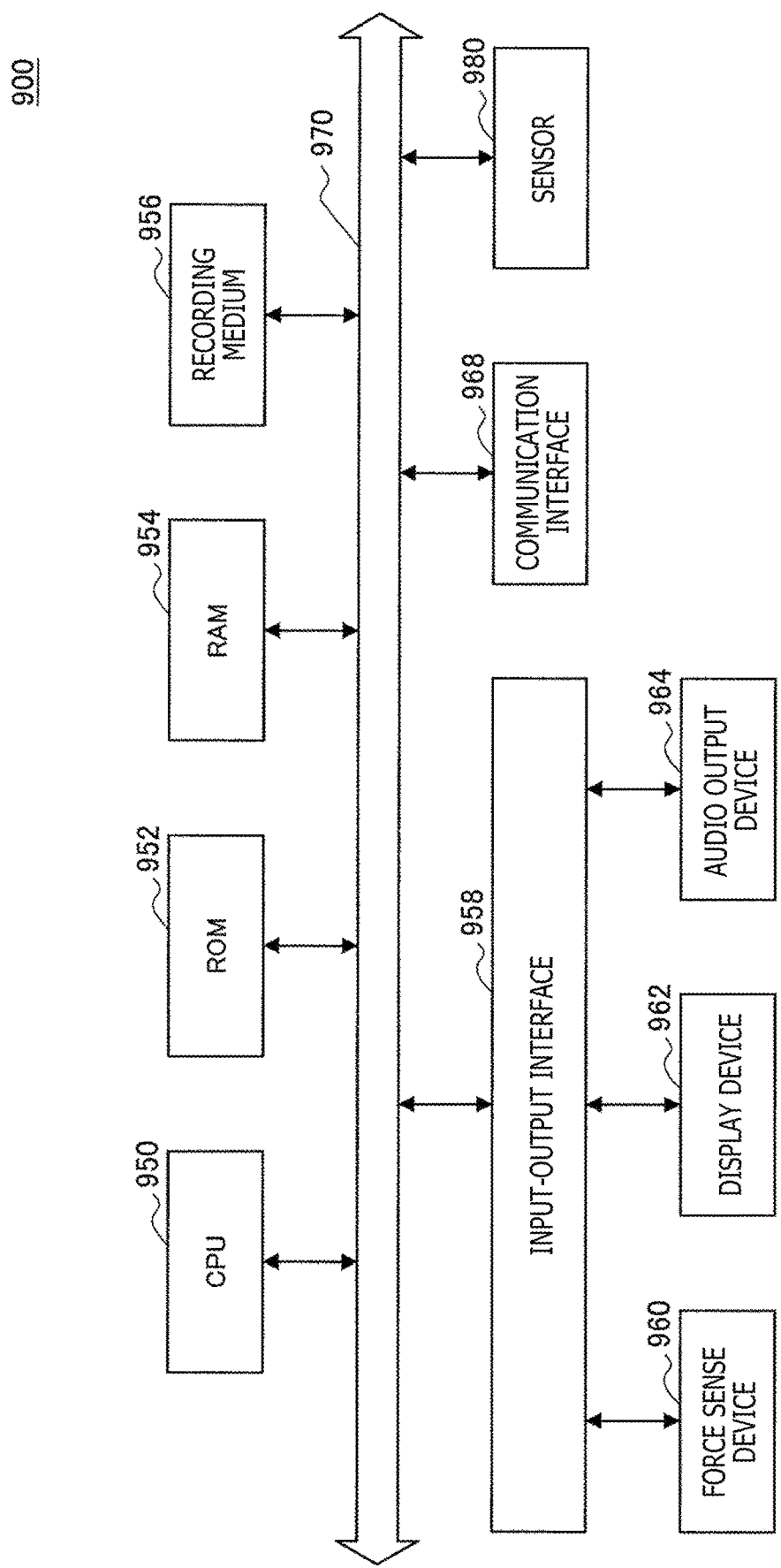
FIG. 31 is a diagram of assistance in explaining an example of a hardware configuration of an information processing device 900 according to an embodiment of the present disclosure.

FIG. 31 is a diagram of assistance in explaining an example of a hardware configuration of an information processing device 900 according to the present embodiment. In FIG. 31, the information processing device 900 represents an example of a hardware configuration of the above-described server 30.

The information processing device 900, for example, includes a CPU 950, a ROM 952, a RAM 954, a recording medium 956, and an input-output interface 958. The information processing device 900 further includes a force sense device 960, a display device 962, an audio output device 964, a communication interface 968, and a sensor 980. In addition, the information processing device 900, for example, establishes connection between the constituent elements by a bus 970 as a data transmission line.
(CPU 950)

The CPU 950 includes, for example, one or two or more processors including an arithmetic circuit such as a CPU or the like, various kinds of processing circuits, or the like. The CPU 950 functions as the main control section 310 that controls the whole of the information processing device 900.
(ROM 952 and RAM 954)

The ROM 952 stores a program used by the CPU 950, control data such as operation parameters and the like, and the like. The RAM 954, for example, temporarily stores the program executed by the CPU 950 and the like. The ROM 952 and the RAM 954 perform functions of the above-described storage section 340, for example, in the information processing device 900.
(Recording Medium 956)

The recording medium 956 functions as the above-described storage section 340. The recording medium 956, for example, stores a variety of data such as data related to the information processing method according to the present embodiment, various kinds of applications, and the like. Here, the recording medium 956 includes, for example, a magnetic recording medium such as a hard disk or the like and a nonvolatile memory such as a flash memory or the like. In addition, the recording medium 956 may be detachable from the information processing device 900.
(Input-Output Interface 958, Force Sense Device 960, Display Device 962, and Audio Output Device 964)

The input-output interface 958, for example, connects the force sense device 960, the display device 962, the audio output device 964, and the like. The input-output interface 958 includes, for example, a USB (Universal Serial Bus) terminal, a DVI (Digital Visual Interface) terminal, an HDMI (High-Definition Multimedia Interface) (registered trademark) terminal, various kinds of processing circuits, and the like.

The force sense device 960 functions as the force sense mechanism 560 of the above-described feedback device 50. The display device 962 functions as the display section 570 of the feedback device 50. The audio output device 964 functions as the audio output section 580 of the feedback device 50. The display device 962 includes, for example, a liquid crystal display, an organic EL display (Organic Electro-Luminescence Display), and the like.

Incidentally, it is needless to say that the input-output interface 958 can be connected to external devices such as operating input devices (for example, a keyboard, a mouse, and the like) external to the information processing device 900, display devices external to the information processing device 900, and the like.

(Communication Interface 968)

The communication interface 968 is communicating means functioning as the communicating section 330 and provided to the information processing device 900. The communication interface 968 functions as a communicating unit for communicating with an external device via a network (or directly) in a wireless or wired manner. Here, the communication interface 968 includes, for example, a communication antenna and an RE (Radio Frequency) circuit (wireless communication), an IEEE 802.15.1 port and a transmitting and receiving circuit (wireless communication), an IEEE 802.11 port and a transmitting and receiving circuit (wireless communication), a LAN (Local Area Network) terminal and a transmitting and receiving circuit (wired communication), or the like.

An example of the hardware configuration of the information processing device 900 has been illustrated above. It is to be noted that the hardware configuration of the information processing device 900 is not limited to the configuration illustrated in FIG. 31. Specifically, the above-described constituent elements may be formed by using a general-purpose member, or may include hardware specialized for the functions of the respective constituent elements. Such a configuration can be changed as appropriate according to the level of the current technology being ca tried out.

For example, the information processing device 900 may not include the communication interface 968 in a case where the information processing device 900 communicates with an external device or the like via a connected external communication device or in a case where the information processing device 900 is configured to perform processing on a stand-alone basis. In addition, the communication interface 968 may have a configuration capable of communicating with one or two or more external devices by a plurality of communication systems.

In addition, the information processing device according to the present embodiment may be applied to a system including a plurality of devices and assuming connection to a network (or communication between devices) as in, for example, cloud computing or the like. That is, the information processing device according to the foregoing present embodiment can also be implemented, for example, as an information processing system that performs processing of the information processing method according to the present embodiment by a plurality of devices.

4. Supplement

It is to be noted that the embodiment of the present disclosure described earlier can, for example, include a program for making a computer function as the information processing device according to the present embodiment and a non-transient tangible medium on which the program is recorded. In addition, the program may be distributed via a communication line such as the Internet or the like (including wireless communication).

In addition, each step in the information processing method according to the embodiment of the present disclosure described above may not necessarily be processed is the described order. For example, each step may be processed in the order changed as appropriate. In addition, each step may be partly processed in parallel or individually instead of being processed in time series. Further, the processing method of each step may not necessarily be processed by the described method either, but may, for example, be processed by another method by another functional section.

A preferred embodiment of the present disclosure has been described above in detail with reference to the accompanying drawings. However, the technical scope of the present disclosure is not limited to such an example. It is obvious that a person having an ordinary knowledge in the technical field of the present disclosure could conceive of various changes or modifications within the scope of technical concepts described in claims. It is therefore to be understood that these changes or modifications also naturally fall within the technical scope of the present disclosure.

In addition, effects described in the present specification are merely exemplary or illustrative, and are not restrictive. That is, the technology according to the present disclosure can produce other effects obvious to those skilled in the art from the description of the present specification together with the above-described effects or in place of the above-described effects. That is, the above-described effects are not necessarily restrictive, but other effects that can be recognized from the present specification may be produced together with the above-described effects or in place of the above-described effects.

It is to be noted that the following configurations also belong to the technical scope of the present disclosure.

(1)

An information processing device including:
  a sensing data obtaining section configured to obtain sensing data regarding at least one of a motion pattern, a motion speed, a motion accuracy, and a motion amount of a motion element of a user in a practice in performance performed by movement of at least a part of a body of the user and a state of a result produced by the performance;
  an analyzing section configured to analyze the obtained sensing data and estimate information regarding the practice in the performance of the user on the basis of a result of the analysis; and
  an output section configured to output a result of the estimation to the user.

(2)

The information processing device according to the above (1), in which
  the information regarding the practice includes at least one of a practice time, a break time, timing of a break of the user, and a practice menu.

(3)

The information processing device according to the above (1) or (2), in which
  the analyzing section estimates a break to be taken by the user on the basis of a temporal change in a motion function of the user, the temporal change being obtained from the sensing data.

(4)

The information processing device according to any one of the above (1) to (3), in which
the analyzing section estimates at least one of a break and a practice to be taken and performed by the user on the basis of a practice time for each type of the practice, the practice time being obtained from the sensing data.

(5)

The information processing device according to any one of the above (1) to (4), in which
the analyzing section estimates a practice to be performed by the user on the basis of a temporal change in learning conditions of the performance of the user, the temporal change being obtained from the sensing data.

(6)

The information processing device according to the above (2), in which
the practice menu includes a training menu for improving a motion function or a sensory function of a skill related to the performance.

(7)

The information processing device according to the above (5), in which
the analyzing section estimates the practice to be performed by the user on the basis of learning conditions of a skill related to the performance, the learning conditions being obtained from the sensing data.

(8)

The information processing device according to the above (1), in which
the analyzing section collects sound related to the practice in the performance of the user, and estimates the practice of the user on the basis of the collected sound.

(9)

The information processing device according to the above (1), in which
the output section outputs the information obtained from the analyzing section to the user by at least one of displaying a predetermined image by controlling a display device, providing tactile stimulation to the user by controlling a wearable device fitted to the body of the user, and outputting a predetermined sound by controlling an audio output device.

(10)

The information processing device according to the above (9), in which
the display device includes a display device configured to display a predetermined virtual object as augmented reality in a state of being superimposed on a real space.

(11)

The information processing device according to the above (10), in which
the display device displays a plurality of spectators as the virtual object.

(12)

The information processing device according to the above (10), in which
the display device displays an inside of a musical instrument played by the user as the virtual object.

(13)

The information processing device according to the above (10), in which
the display device changes size of a musical note displayed on a score according to an interpretation of sound by the user.

(14)

The information processing device according to the above (1), in which
the sensing data includes at least one of pieces of sensing data obtained from an acceleration sensor, a gyro sensor, an angular velocity sensor, a vibration sensor, a pressure sensor, a biological information sensor, a bending sensor, and a position sensor that are fitted to the user.

(15)

The information processing device according to the above (14), in which
the bending sensor includes a fingerstall type bending sensor fitted to a fingertip of the user.

(16)

The information processing device according to the above (1), in which
the sensing data includes sensing data obtained from a pressure sensor or a photoreflector sensor configured to sense movement of a target object moved by operation of the user, the pressure sensor or the photoreflector sensor being mounted in the target object, or sensing data obtained from the target object according to the operation of the user.

(17)

The information processing device according to the above (16), in which
the target object includes an acoustic musical instrument or an electronic musical instrument or an electronic apparatus related to playing.

(18)

The information processing device according to the above (1), in which
the sensing data includes at least one of pieces of sensing data obtained from an imaging device configured to image the user, a nuclear magnetic resonance sensor configured to sense nuclear magnetic resonance in the user, and a sound collecting device configured to collect a sound produced by the performance or a voice uttered from the user or a person around the user.

(19)

An information processing method including:
obtaining sensing data regarding at least one of a motion pattern, a motion speed, a motion accuracy, and a motion amount of a motion element of a user in a practice in performance performed by movement of at least a part of a body of the user and a state of a result produced by the performance;
analyzing the obtained sensing data and estimating information regarding the practice in the performance of the user on the basis of a result of the analysis; and
outputting a result of the estimation to the user.

(20)

A program for causing a computer to realize:
a function of obtaining sensing data regarding at least one of a motion pattern, a motion speed, a motion accuracy, and a motion amount of a motion element of a user in a practice in performance performed by movement of at least a part of a body of the user and a state of a result produced by the performance;
a function of analyzing the obtained sensing data and estimating information regarding the practice in the performance of the user on the basis of a result of the analysis; and a function of outputting a result of the estimation to the user.

REFERENCE SIGNS LIST

1: Information processing platform
10: Sensor device
10a, 10d: Microphone
10b: Biological information sensor
10c: MIDI terminal
10e: Fingerstall type sensor device
30: Server
50: Feedback device
50a: Display
50b: Speaker
50c: Force sense robot
50d: Smart glass
100: Sensor section
110, 310, 510: Main control section
112, 312: Data obtaining section
114, 314: Processing section
116, 316: Output control section.
130, 330, 530: Communicating section
150: Ring member
160: Bending sensor member
170: Fixing member
180: Wiring
190: Terminal
320: Output section
340, 540: Storage section
500: Camera
560: Force sense mechanism
570: Display section
572: Display unit
580: Audio output section.
600, 610, 620, 630, 640, 650, 660, 680, 700, 710, 720, 730, 740, 750, 760, 820: Screen display
602: Circle graph
604: Bar graph
606: Title display
612a, 612b, 612c, 624, 626, 634, 636, 658, 714a, 714b, 716a, 716b, 734, 736, 738, 822a, 822b, 822c: Button
622, 632, 666, 668, 686, 688, 712, 722, 732, 744, 752: Window display
642, 644, 652, 702: Score display
654, 670, 690, 706: Frame
656a, 656b, 704: Cursor
662, 682: Keyboard display
664, 684: Temporal change display
708: Moving image display
724: Point display
742: Ranking display
800, 802: Marker
810: Animation
900: Information processing device
950: CPU
952: ROM
954: RAM
956: Recording medium.
958: Input-output interface
960: Force sense device
962: Display device
964: Audio output device
968: Communication interface
970: Bus
980: Sensor

The invention claimed is:

1. An information processing device comprising:
a sensing data obtaining section configured to
obtain sensing data regarding at least one of a motion pattern, a motion speed, a motion accuracy, or a motion amount of a motion element of at least one part of a body of a user during practice performed by movement of the at least one part of the body of the user, and
obtain a result produced by the practice;
an analyzing section configured to
analyze the obtained sensing data, and
estimate information regarding the practice of the user based on a result of the analysis; and
an output section configured to output a result of the estimation to the user,
wherein the output section outputs the result of the estimation by using a force sense mechanism to provide feedback related to the sensing data obtained from the analyzing section, and
wherein the sensing data obtaining section, the analyzing section, and the output section are each implemented via at least one processor.

2. The information processing device according to claim 1, wherein
the information regarding the practice includes at least one of a practice time, a break time, timing of a break of the user, or a practice menu.

3. The information processing device according to claim 2, wherein
the practice menu includes a training menu for improving a motion function or a sensory function of a skill related to the practice.

4. The information processing device according to claim 1, wherein
the analyzing section estimates the information regarding the practice by estimating a break to be taken by the user based on a temporal change in the motion element of the at least one part of the body of the user, the temporal change being obtained from the sensing data.

5. The information processing device according to claim 1, wherein
the analyzing section estimates the information regarding the practice by estimating at least one of a break or a practice to be taken and performed by the user based on a practice time for each type of the practice, the practice time being obtained from the sensing data.

6. The information processing device according to claim 1, wherein
the analyzing section estimates the information regarding the practice by estimating a practice to be performed by the user based on a temporal change in learning conditions of the practice of the user, the temporal change being obtained from the sensing data.

7. The information processing device according to claim 6, wherein
the analyzing section estimates the practice to be performed by the user based on learning conditions of a skill related to the practice, the learning conditions being obtained from the sensing data.

8. The information processing device according to claim 1, wherein
the analyzing section
analyzes the obtained sensing data based on collected sound related to the practice of the user, and
estimates the information regarding the practice of the user based on the collected sound.

9. The information processing device according to claim 1, wherein
the output section further outputs the result of the estimation by outputting the information obtained from the analyzing section to the user by at least one of displaying a predetermined image by controlling a display device, providing tactile stimulation to the user by controlling a wearable device fitted to the at least one part of the body of the user, or outputting a predetermined sound by controlling an audio output device.

10. The information processing device according to claim 9, wherein
the display device includes a display device configured to display a predetermined virtual object as augmented reality in a state of being superimposed on a real space.

11. The information processing device according to claim 10, wherein
the display device displays a plurality of spectators as the virtual object.

12. The information processing device according to claim 10, wherein
the display device displays an inside of a musical instrument played by the user as the virtual object.

13. The information processing device according to claim 10, wherein
the display device changes size of a musical note displayed on a score according to an interpretation of sound by the user.

14. The information processing device according to claim 1, wherein
the sensing data includes at least one of pieces of sensing data obtained from an acceleration sensor, a gyro sensor, an angular velocity sensor, a vibration sensor, a pressure sensor, a biological information sensor, a bending sensor, or a position sensor fitted to the user.

15. The information processing device according to claim 14, wherein
the bending sensor includes a fingerstall type bending sensor fitted to a fingertip of the user.

16. The information processing device according to claim 1, wherein
the sensing data includes at least one of
sensing data obtained from a pressure sensor or a photoreflector sensor configured to sense movement of a target object moved by operation of the user, the pressure sensor or the photoreflector sensor being mounted in the target object, or
sensing data obtained from the target object according to the operation of the user.

17. The information processing device according to claim 16, wherein
the target object includes an acoustic musical instrument or an electronic musical instrument or an electronic apparatus related to playing.

18. The information processing device according to claim 1, wherein
the sensing data includes at least one of pieces of sensing data obtained from an imaging device configured to image the user, a nuclear magnetic resonance sensor configured to sense nuclear magnetic resonance in the user, or a sound collecting device configured to collect a sound produced by the practice or a voice uttered from at least one of the user or a person around the user.

19. An information processing method, executed by at least one processor, the method comprising:
obtaining sensing data regarding at least one of a motion pattern, a motion speed, a motion accuracy, or a motion amount of a motion element of at least one part of a body of a user during practice performed by movement of the at least one part of the body of the user;
obtaining a result produced by the practice;
analyzing the obtained sensing data;
estimating information regarding the practice of the user based on a result of the analysis; and
outputting a result of the estimation to the user,
wherein the result of the estimation is output by using a force sense mechanism to provide feedback related to the obtained sensing data.

20. A non-transitory computer-readable storage medium having embodied thereon a program, which when executed by a computer causes the computer to execute a method, the method comprising:
obtaining sensing data regarding at least one of a motion pattern, a motion speed, a motion accuracy, or a motion amount of a motion element of at least one part of a body of a user during practice performed by movement of the at least one part of the body of the user;
obtaining a result produced by the practice;
analyzing the obtained sensing data;
estimating information regarding the practice in the performance of the user based on a result of the analysis; and
outputting a result of the estimation to the user,
wherein the result of the estimation is output by using a force sense mechanism to provide feedback related to the obtained sensing data.

* * * * *